(12) United States Patent
Dershem

(10) Patent No.: US 7,928,153 B2
(45) Date of Patent: Apr. 19, 2011

(54) THERMOSETTING POLYETHER OLIGOMERS, COMPOSITIONS AND METHODS FOR USE THEREOF

(75) Inventor: Stephen M Dershem, San Diego, CA (US)

(73) Assignee: Designer Molecules, Inc., San Diego, CA (US)

( * ) Notice: Subject to any disclaimer, the term of this patent is extended or adjusted under 35 U.S.C. 154(b) by 102 days.

(21) Appl. No.: 12/192,058

(22) Filed: Aug. 14, 2008

(65) Prior Publication Data

US 2009/0061244 A1    Mar. 5, 2009

Related U.S. Application Data

(63) Continuation of application No. 60/964,800, filed on Aug. 14, 2007.

(51) Int. Cl.
*C08K 3/10* (2006.01)
(52) U.S. Cl. .................... 524/403; 528/80; 528/425
(58) Field of Classification Search .............. 524/403; 528/86, 425
See application file for complete search history.

(56) References Cited

U.S. PATENT DOCUMENTS

| | | | |
|---|---|---|---|
| 3,918,393 A * | 11/1975 | Hahn ......................... 427/494 |
| 4,968,738 A * | 11/1990 | Dershem |
| 5,045,127 A * | 9/1991 | Dershem et al. |
| 5,064,480 A * | 11/1991 | Dershem et al. |
| 5,155,177 A * | 10/1992 | Frihart |
| 5,232,962 A * | 8/1993 | Dershem et al. |
| 5,306,333 A * | 4/1994 | Dershem et al. |
| 5,358,992 A * | 10/1994 | Dershem et al. |
| 5,403,389 A * | 4/1995 | Dershem |
| 5,430,112 A * | 7/1995 | Sakata et al. |
| 5,447,988 A * | 9/1995 | Dershem et al. |
| 5,489,641 A * | 2/1996 | Dershem |
| 5,567,761 A * | 10/1996 | Song |
| 5,646,241 A * | 7/1997 | Dershem et al. |
| 5,714,086 A * | 2/1998 | Osuna et al. |
| 5,717,034 A | 2/1998 | Dershem et al. |
| 5,718,941 A | 2/1998 | Dershem et al. |
| 5,753,748 A | 5/1998 | Dershem et al. |
| 5,861,111 A | 1/1999 | Dershem et al. |
| 5,969,036 A | 10/1999 | Dershem |
| 5,973,166 A | 10/1999 | Mizori et al. |
| 6,034,150 A | 3/2000 | Hoyle et al. |
| 6,034,194 A | 3/2000 | Dershem |
| 6,034,195 A | 3/2000 | Dershem |
| 6,048,953 A | 4/2000 | Kawashima et al. |
| 6,121,358 A | 9/2000 | Dershem et al. |
| 6,187,886 B1 | 2/2001 | Husson et al. |
| 6,211,320 B1 | 4/2001 | Dershem et al. |
| 6,300,456 B1 | 10/2001 | Musa |
| 6,369,124 B1 | 4/2002 | Hoyle et al. |
| 6,423,780 B1 | 7/2002 | Dershem et al. |
| 6,429,281 B1 | 8/2002 | Dershem et al. |
| 6,521,731 B2 | 2/2003 | Dershem et al. |
| 6,620,946 B2 | 9/2003 | Dershem et al. |
| 6,743,852 B2 | 6/2004 | Dershem et al. |
| 6,750,301 B1 | 6/2004 | Bonneau et al. |
| 6,790,597 B2 | 9/2004 | Dershem |
| 6,825,245 B2 | 11/2004 | Dershem |
| 6,831,132 B2 | 12/2004 | Liu et al. |
| 6,852,814 B2 | 2/2005 | Dershem et al. |
| 6,855,745 B2 | 2/2005 | Hoyle et al. |
| 6,916,856 B2 | 7/2005 | Dershem |
| 6,946,523 B2 | 9/2005 | Dershem et al. |
| 6,960,636 B2 | 11/2005 | Dershem et al. |
| 6,963,001 B2 | 11/2005 | Dershem et al. |
| 7,102,015 B2 | 9/2006 | Dershem et al. |
| 7,157,587 B2 | 1/2007 | Mizori et al. |
| 7,176,044 B2 | 2/2007 | Forray et al. |
| 7,199,249 B2 | 4/2007 | Liu et al. |
| 7,208,566 B2 | 4/2007 | Mizori et al. |
| 7,285,613 B2 | 10/2007 | Dershem et al. |
| 7,309,724 B2 | 12/2007 | Dershem et al. |
| 7,517,925 B2 | 4/2009 | Dershem et al. |
| 7,678,879 B2 | 3/2010 | Dershem |
| 2002/0062923 A1 | 5/2002 | Forray |
| 2002/0099168 A1 | 7/2002 | Dershem et al. |
| 2002/0188137 A1 | 12/2002 | Dershem et al. |
| 2002/0193541 A1 | 12/2002 | Dershem et al. |
| 2002/0198356 A1 | 12/2002 | Dershem et al. |
| 2003/0008992 A1 | 1/2003 | Dershem et al. |
| 2003/0055121 A1 | 3/2003 | Dershem et al. |

(Continued)

FOREIGN PATENT DOCUMENTS

EP    1156036    11/2001

(Continued)

OTHER PUBLICATIONS

Andersson et al., "Initiator-Free Photopolymerization of an Aliphatic Vinyl Ether-Maleimide Monomer", *J Coatings Tech* 69: 1997, 91-95.

(Continued)

*Primary Examiner* — Edward J Cain

(74) *Attorney, Agent, or Firm* — The Law Office of Jane K. Babin, Professional Corporaton; Jane K. Babin

(57) ABSTRACT

The invention is based on the discovery that certain polyether oligomers bearing curable moieties are useful as adhesives for the microelectonic packaging industry. Specifically, certain thermoset adhesive compositions containing polyether oligomers of the invention have good adhesion with lower viscosity, lower resistivity, higher conductivity and higher thixotropy when compared to acrylate- and maleimide-based thermoset adhesives.

41 Claims, No Drawings

U.S. PATENT DOCUMENTS

| | | |
|---|---|---|
| 2003/0060531 A1 | 3/2003 | Dershem et al. |
| 2003/0083436 A1 | 5/2003 | Deitch |
| 2003/0087999 A1 | 5/2003 | Dershem et al. |
| 2003/0109666 A1 | 6/2003 | Dershem et al. |
| 2003/0125551 A1 | 7/2003 | Dershem et al. |
| 2003/0199638 A1 | 10/2003 | Liu et al. |
| 2003/0208016 A1 | 11/2003 | Dershem et al. |
| 2004/0006166 A1 | 1/2004 | Liu et al. |
| 2004/0019224 A1 | 1/2004 | Dershem et al. |
| 2004/0077798 A1 | 4/2004 | Dershem et al. |
| 2004/0082724 A1 | 4/2004 | Dershem et al. |
| 2004/0099331 A1 | 5/2004 | Buckner |
| 2004/0102566 A1 | 5/2004 | Forray et al. |
| 2004/0123948 A1 | 7/2004 | Dershem et al. |
| 2004/0225026 A1 | 11/2004 | Mizori et al. |
| 2004/0225045 A1 | 11/2004 | Forray |
| 2004/0225059 A1 | 11/2004 | Mizori et al. |
| 2005/0027082 A1 | 2/2005 | Narayan-Sarathy et al. |
| 2005/0107542 A1* | 5/2005 | Liu et al. |
| 2005/0136620 A1* | 6/2005 | Dershem et al. |
| 2005/0137277 A1* | 6/2005 | Dershem et al. |
| 2005/0267254 A1* | 12/2005 | Mizori et al. |
| 2005/0272888 A1* | 12/2005 | Dershem et al. |
| 2006/0009570 A1* | 1/2006 | Zychowski |
| 2006/0009578 A1* | 1/2006 | Dershem |
| 2006/0063014 A1* | 3/2006 | Forray |
| 2006/0069232 A1* | 3/2006 | Dershem |
| 2006/0142517 A1* | 6/2006 | Dershem |
| 2007/0155869 A1* | 7/2007 | Dershem et al. |
| 2007/0205399 A1* | 9/2007 | Mizori |
| 2007/0299154 A1* | 12/2007 | Dershem et al. |
| 2008/0017308 A1* | 1/2008 | Dershem et al. |
| 2008/0075961 A1* | 3/2008 | Mizori |
| 2008/0075963 A1* | 3/2008 | Dershem |
| 2008/0075965 A1* | 3/2008 | Dershem |
| 2008/0103240 A1* | 5/2008 | Dershem |
| 2008/0142158 A1* | 6/2008 | Dershem |
| 2008/0146738 A1* | 6/2008 | Dershem |
| 2008/0160315 A1* | 7/2008 | Forray et al. |
| 2008/0191173 A1* | 8/2008 | Dershem et al. |
| 2008/0210375 A1* | 9/2008 | Dershem et al. |
| 2008/0251935 A1* | 10/2008 | Dersham |
| 2008/0257493 A1* | 10/2008 | Dershem |
| 2008/0262191 A1* | 10/2008 | Mizori |
| 2009/0061244 A1* | 3/2009 | Dershem |
| 2009/0215940 A1* | 8/2009 | Dershem |
| 2009/0288768 A1* | 11/2009 | Dershem |
| 2010/0041803 A1* | 2/2010 | Dershem |
| 2010/0041823 A1* | 2/2010 | Dershem |
| 2010/0041832 A1* | 2/2010 | Dershem |
| 2010/0041845 A1* | 2/2010 | Dershem et al. |
| 2010/0056671 A1* | 3/2010 | Dershem |
| 2010/0063184 A1* | 3/2010 | Dershem |

FOREIGN PATENT DOCUMENTS

| | | |
|---|---|---|
| JP | 2003002919 | 1/2003 |
| WO | WO-9406862 | 3/1994 |
| WO | WO-2005121190 | 12/2005 |
| WO | WO-2007100329 | 9/2007 |
| WO | WO-2008077141 | 6/2008 |
| WO | WO-2008030894 | 10/2008 |
| WO | WO-2008124797 | 10/2008 |
| WO | WO-2010019832 | 2/2010 |

OTHER PUBLICATIONS

Kohli et al., "Co-Polymerization of Maleimides and Vinyl Ethers: A Structural Study", *Macromolecules* 31: 1998, 5681-5689.

* cited by examiner

THERMOSETTING POLYETHER OLIGOMERS, COMPOSITIONS AND METHODS FOR USE THEREOF

RELATED APPLICATIONS

The present application claims the benefit of priority under 35 U.S.C. §119 to U.S. Provisional Application No. 60/964,800 filed Aug. 14, 2007, the entire contents of which are incorporated herein by reference.

FIELD OF THE INVENTION

The present invention relates to thermosetting adhesive compositions and uses therefor. In particular, the present invention relates to thermosetting polyether compounds, polyether oligomers and compositions containing curable polyether compounds and oligomers.

BACKGROUND OF THE INVENTION

Adhesives, particularly conductive adhesives, are used for a variety of purposes in the fabrication and assembly of semiconductor packages and microelectronic devices. The more prominent uses include bonding of electronic elements such as integrated circuit chips to lead frames or other substrates, and bonding of circuit packages or assemblies to printed wire boards. Adhesives useful for electronic packaging applications typically exhibit properties such as good mechanical strength, curing properties that do not affect the component or the carrier, and thixotropic properties compatible with application to microelectronic and semiconductor components. In addition, such adhesives must be able to withstand local temperature fluctuations present during use of e.g., a circuit board without losing strength or adhesiveness, and should not be hydrophilic because absorption of atmospheric moisture can also degrade strength and adhesiveness during thermal cycling.

Thermoset compounds that are useful for microelectronic adhesives include (meth)acrylate monomers. These compounds are typically polymerized by means of free radical initiators. This is a rapid reaction and this type of cure is well suited for high-throughput industrial processes.

Monomer backbones containing ether linkages are attractive because of their superior hydrolytic resistance. However, only a limited range of (meth)acrylate monomers with polyether backbones are currently available. Commercially available polyether-based (meth)acrylate monomers fall into three general categories: derivatives of polyethylene glycol, derivatives of polypropylene glycol, and ethylene oxide adducts of bisphenol A. The polyethylene glycol derivatives are much too hydrophilic to be used in microelectronic applications. The polypropylene oxide derivatives are somewhat less hydrophilic, but have poor thermal stability. Some of the bisphenol A derivatives have properties that allow their use in microelectronic adhesives, but others do not. For example, the short chain adducts (i.e. around two moles ethylene oxide (EO) per bisphenol A) have high viscosities (i.e. over 1,000 centipoises), while the long chain adducts (equal to or greater than four moles EO per bisphenol A) are too hydrophilic for most microelectronic applications.

There remains a need therefore for hydrophobic, low viscosity, polyether based monomers that can fill a properties gap that is not met by the materials currently available in the marketplace.

SUMMARY OF THE INVENTION

The present invention provides polyether oligomer s represented by structural formula I:

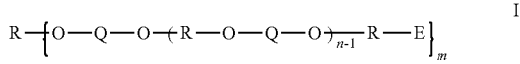

where R and Q are each independently substituted or unsubstituted aliphatic, aryl, or heteroaryl; m is 1 to 4; n is 1 to about 10; and each E is independently acrylate, methacrylate, maleimide, styrenic, vinyl ester, olefin, allyl, vinyl ether, itaconate, fumarate, epoxy, oxetane, oxazoline, benzoxazine, cyanate ester, or propargyl ether. In certain embodiments, E is acrylate, methacrylate, maleimide, styrenic.

In certain aspects, R is a substituted or unsubstituted cycloalkyl having from 3 to about 30 carbon atoms, 5 to about 15 carbon atoms or 6 to about 12 carbon atoms. R can, for example be a substituted or unsubstituted cyclopentyl, cyclohexyl, norbornyl, tetracyclododecyl, or dicyclopentadienyl.

In particular embodiments, Q is a substituted or unsubstituted aryl or heteroaryl having from 6 to about 20 carbon atoms. In other embodiments, Q is a substituted or unsubstituted cycloalkyl. For example, Q can be a substituted or unsubstituted phenyl, naphthyl or norbornenyl. In certain aspects of the invention, the polyether oligomers of the invention have a total oxygen content that is less than about 20% by weight. In yet another embodiment, Q is a linear or branched alkyl chain having from 1 to about 50 carbon atoms.

In further embodiments of the invention, the polyether oligomer can be represented by structural formula II:

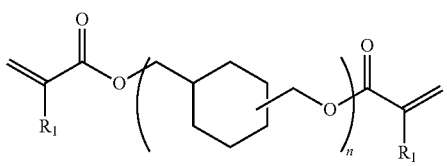

where $R_1$ is H or Me and n is 01-10.

In yet further embodiments of the invention, the polyether oligomer can be represented by structural formula III:

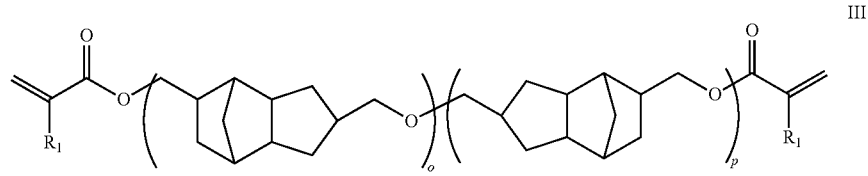

where $R_1$ is H or Me, and (o+p) is 1-10. In certain aspects of formula III, (o+p) is 2-5.

The invention also encompasses polyether oligomers represented by structural formula IV:
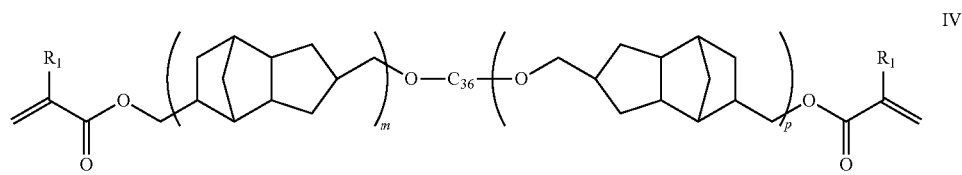
where each $R_1$ is independently H or Me; m and p are each independently 1 to 10; and $C_{36}$ is a dimer diol residue.
The present invention specifically provides polyether compounds that include:
COMPOUND 1
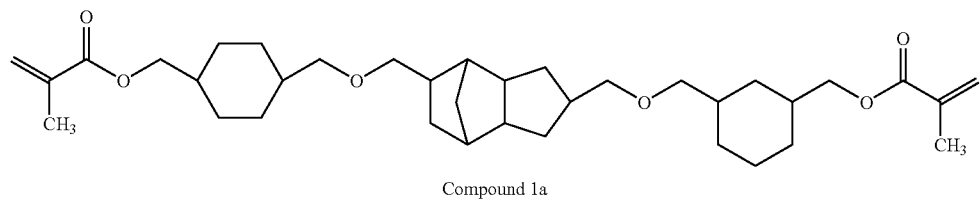
Compound 1a
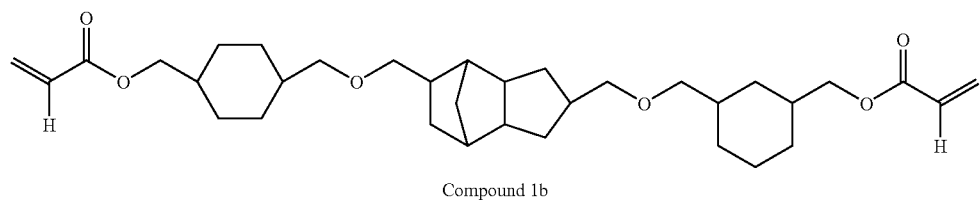
Compound 1b
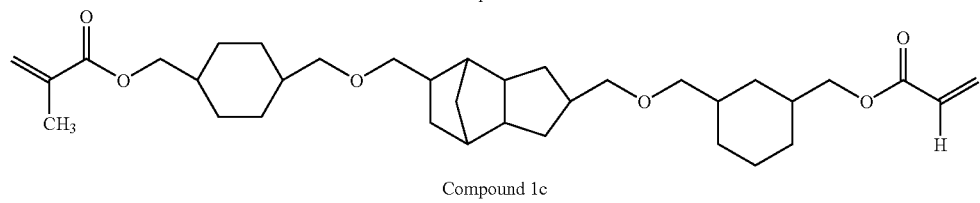
Compound 1c
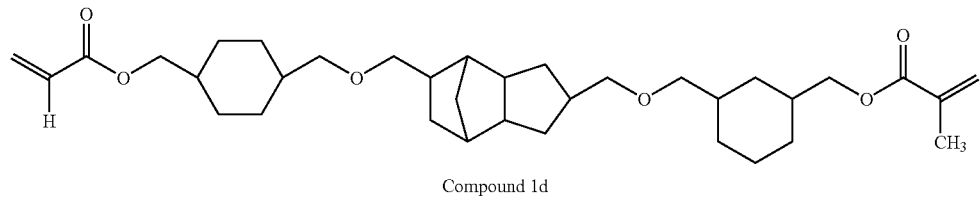
Compound 1d
COMPOUND 2
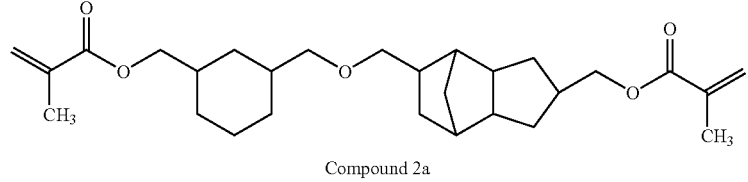
Compound 2a
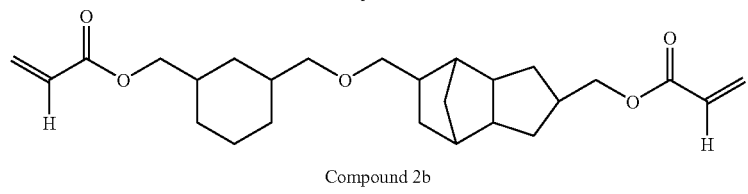
Compound 2b

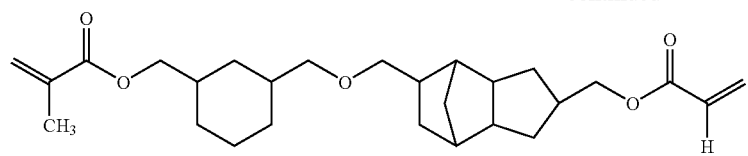
Compound 2c
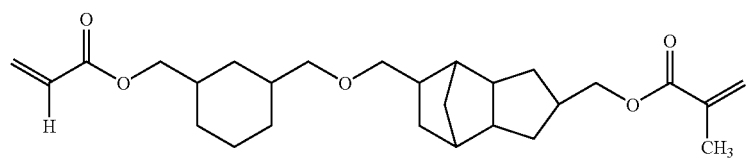
Compound 2d
COMPOUND 3
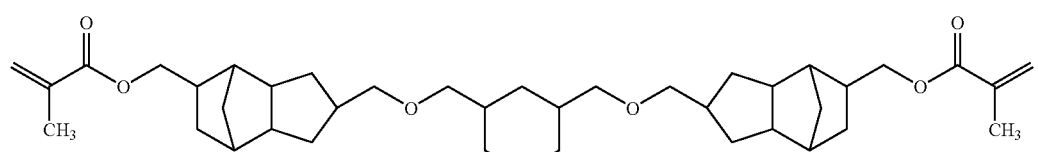
Compound 3a
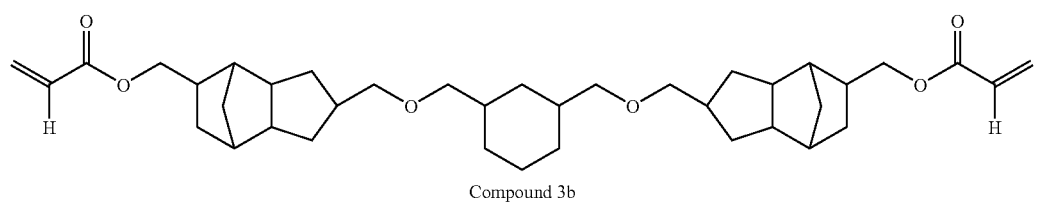
Compound 3b
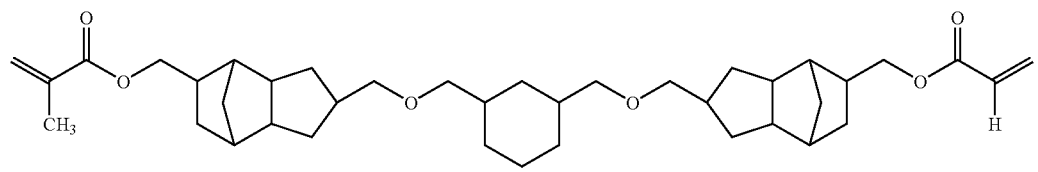
Compound 3c
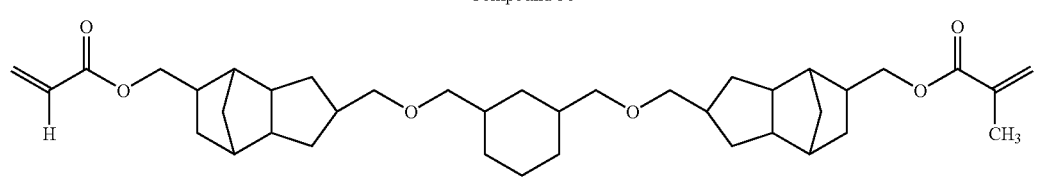
Compound 3d
COMPOUND 4
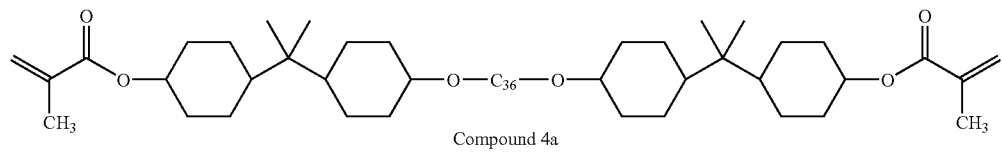
Compound 4a
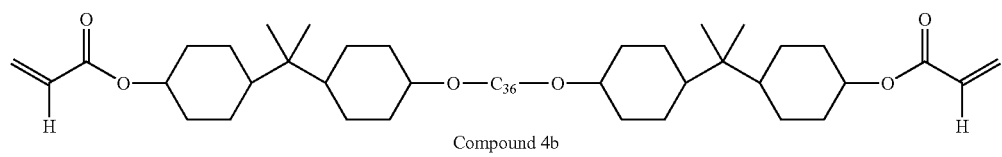
Compound 4b
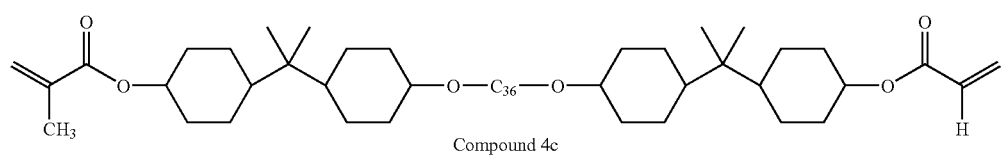
Compound 4c -continued
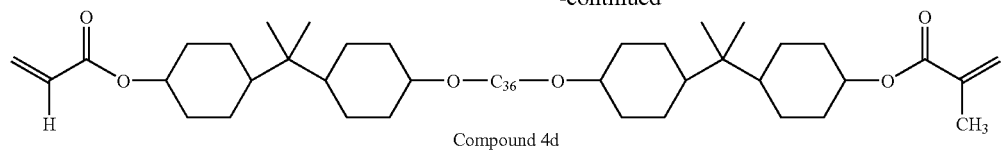
Compound 4d
COMPOUND 5
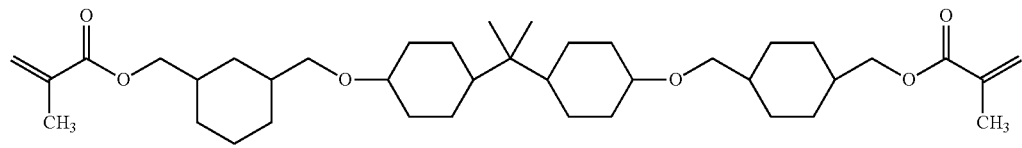
Compound 5a
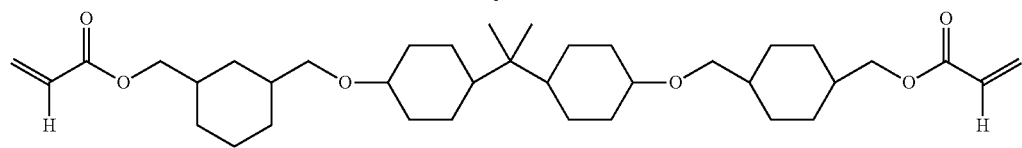
Compound 5b
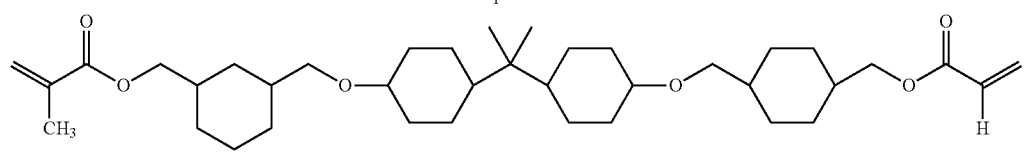
Compound 5c
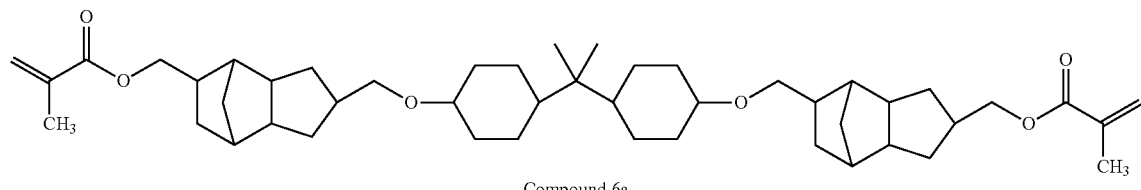
Compound 5d
COMPOUND 6
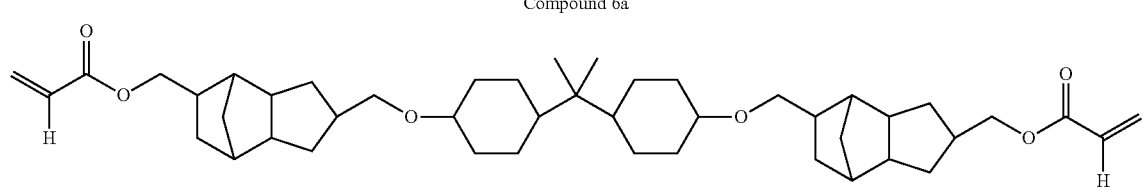
Compound 6a
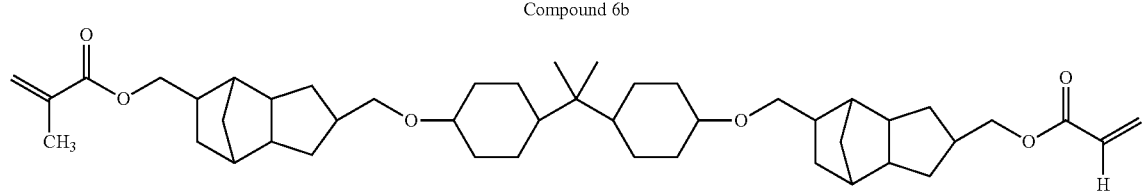
Compound 6b
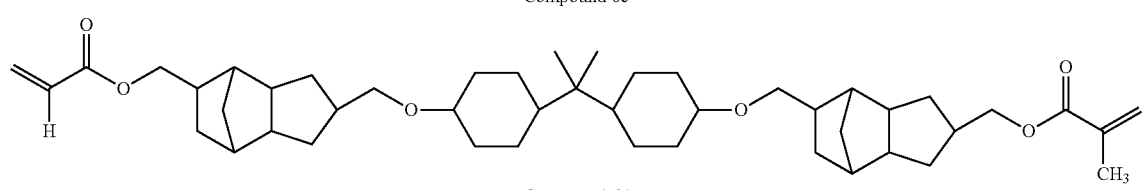
Compound 6c
Compound 6d COMPOUND 7
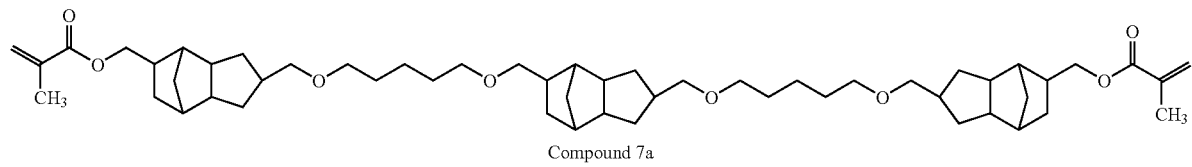
Compound 7a
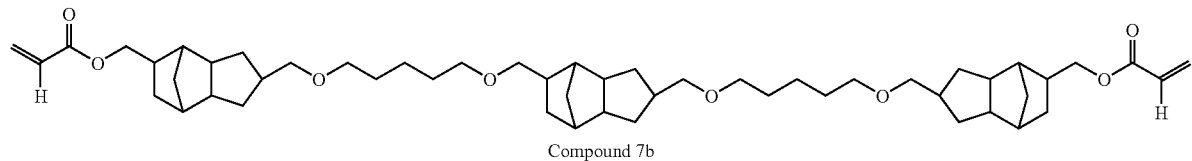
Compound 7b
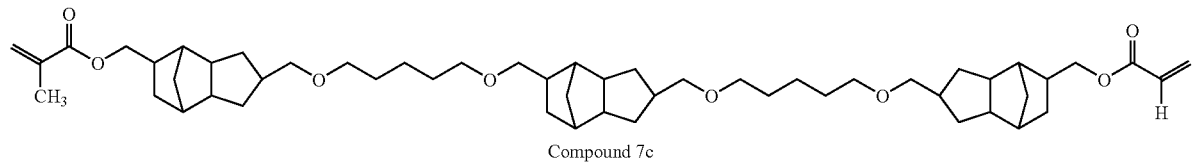
Compound 7c
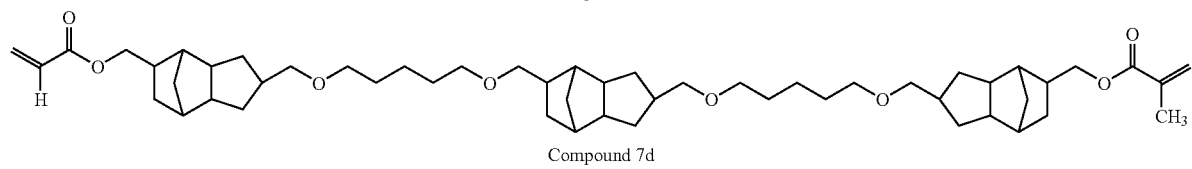
Compound 7d
COMPOUND 8
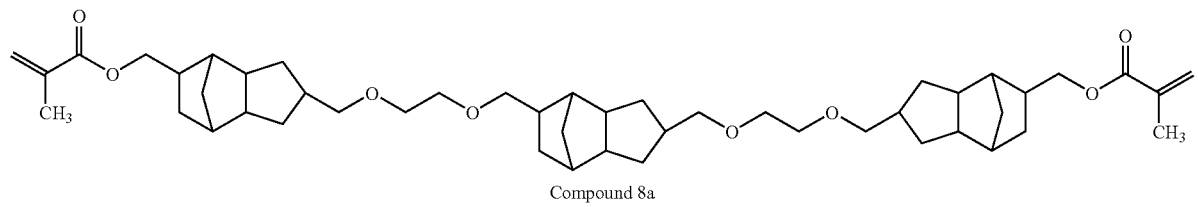
Compound 8a
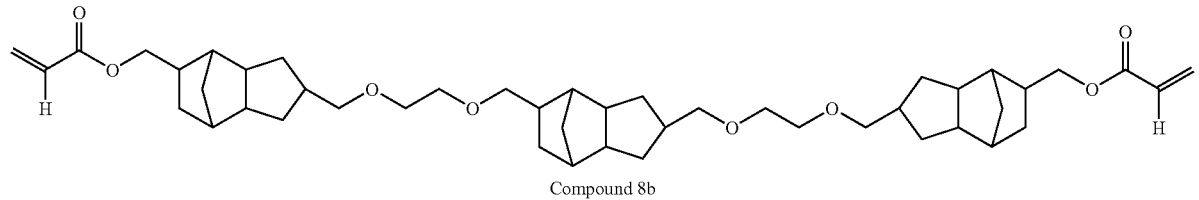
Compound 8b
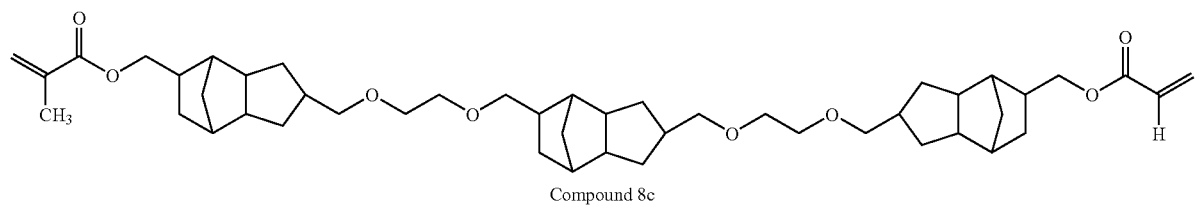
Compound 8c
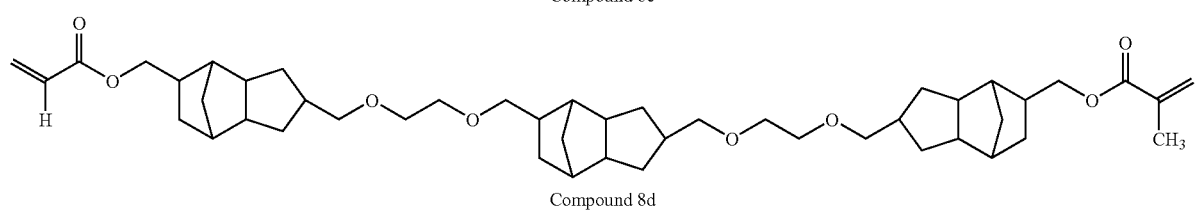
Compound 8d

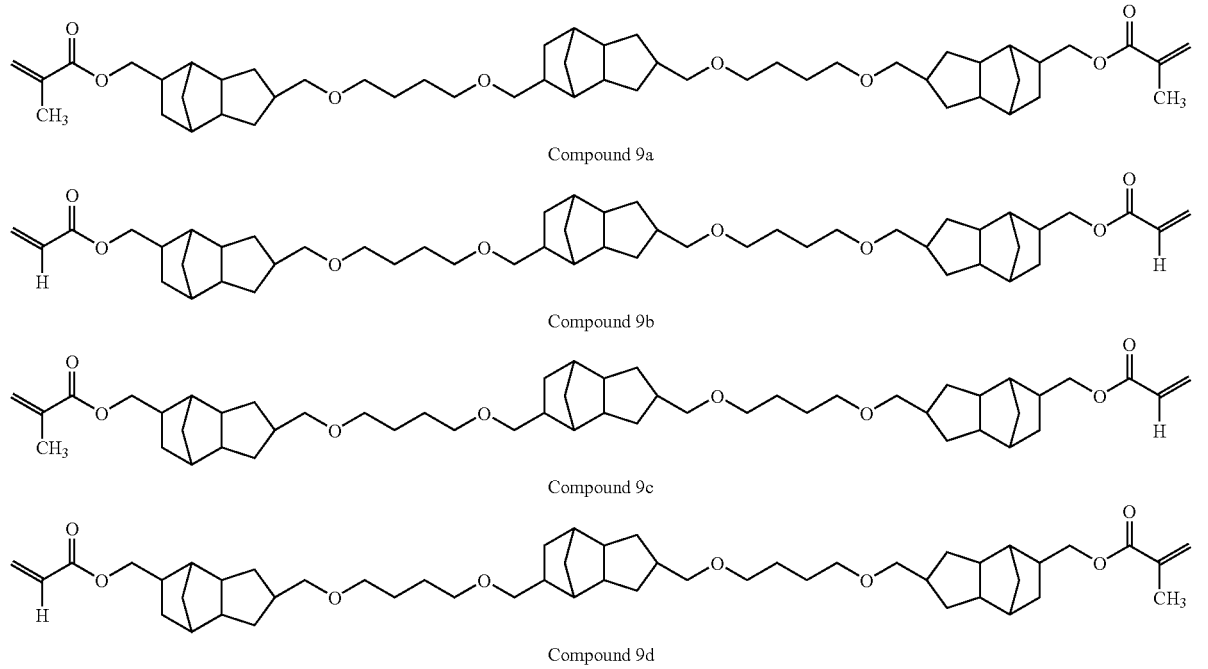

Compound 9a

Compound 9b

Compound 9c

Compound 9d

Also provided by the invention are adhesive compositions that contain at least one polyether oligomer of the invention and at least one curing initiator, which initiator can be present at 0.1 wt % to about 5 wt % based on total weight of the composition. The curing initiator can include, for example, a free-radical initiator, a photoinitiator or both a free-radical initiator and a photoinitiator.

The adhesive compositions can also contain one or more additional compounds such as an acrylate, a methacrylate, a maleimide, a vinyl ether, a vinyl ester, a styrenic compound and an allyl functional compound.

The adhesive compositions can also include reactive diluents and/or fillers, which fillers can be thermally or electrically conductive. In certain embodiments, the filler includes silver. In certain aspects, the adhesive compositions include at least one additional compound such as an acrylate, a methacrylate, a maleimide, a vinyl ether, a vinyl ester, a styrenic compound or an allyl functional compound.

In certain embodiments, the adhesive compositions include: 0.5 weight percent (wt %) to about 98 wt % of at least one oligomer of claim 1; 0 to about 90 wt % of a filler; 0.1 wt % to about 5 wt % of at least one curing initiator; and 0.1 wt % to about 4 wt %, of at least one coupling agent, where each wt % is based on the total weight of the composition.

The coupling agent can, for example, be a silicate ester, a metal acrylate salt, or a titanate. In some aspects the curing initiator can be a peroxide.

Particular adhesive compositions of the invention have a 5 rpm viscosity of 5,000 to about 10,000 centipoises. In one aspect the viscosity of the adhesive composition is less than about 10,000 centipoises.

The adhesive compositions of the invention can have a thixotropic index (the 0.5/5 viscosity ratio) of at least about 5.8, at least about 6 or at least about 6.5, particularly adhesives containing a polyether oligomer according to structural formula II.

In some embodiments, the adhesive compositions of the invention have a viscosity of 5,000 to 20,000 centipoises, and may also have an electrical resistance of less than 0.0001 to 0.000001 Ohm-cm.

Certain adhesive compositions of the invention contain conductive metal, and in some embodiments, the maximum amount of conductive metal in the invention compositions exceeds the amount of conductive metal in a comparable adhesive composition containing an acrylate monomer.

Also provided by the invention are assemblies including a first article adhered to a second article by a cured aliquot of an adhesive composition of the invention.

The present invention further provides methods for adhesively attaching a first article to a second article by applying an aliquot of an adhesive composition of the invention to the first article, the second article or both the first and second articles; contacting the first article and the second article, wherein the first article and the second article are separated only by the applied adhesive composition; and curing the applied adhesive composition, thereby adhesively attaching the first article to the second article. In another embodiment, the invention provides methods for adhesively attaching a first article to a second article applying an aliquot of the adhesive composition of the invention to the first article the second article or both the first and second articles; melting the applied adhesive composition; contacting the first article and the second article, where the first article and the second article are separated only by the applied (melted) adhesive composition; and curing the applied adhesive composition, thereby adhesively attaching first article to a second article.

The first article and the second article can, for example be memory devices, ASIC devices, microprocessors, copper lead frames, Alloy 42 lead frames, semiconductor dies and/or substrates.

Also provided by the invention are methods for reducing the viscosity of a thermoset adhesive by replacing at least one monomer in the thermoset adhesive with at least one polyether oligomer of the invention. Similarly, the invention provides methods for increasing the conductivity of a thermoset adhesive comprising replacing at least one monomer in the thermoset adhesive with at least one invention polyether oligomer, which can include increasing the amount of conductive metal in the thermoset adhesive composition. In yet a further embodiment, the invention provides methods for reducing the electrical resistance of a thermoset adhesive by replacing at least one monomer in the thermoset adhesive with at least one invention polyether oligomer.

DETAILED DESCRIPTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting.

The section headings used herein are for organizational purposes only and are not to be construed as limiting the subject matter described.

Unless specific definitions are provided, the nomenclatures utilized in connection with, and the laboratory procedures and techniques of polymer chemistry, adhesives manufacturing, analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

Definitions

"About" as used herein means that a number referred to as "about" comprises the recited number plus or minus 1-10% of that recited number. For example, "about" 100 degrees can mean 90-110 degrees or as few as 99-101 degrees depending on the situation. Whenever it appears herein, a numerical range such as "1 to 20" refers to each integer in the given range; e.g., "1 to 20 carbon atoms" means that an alkyl group can contain only 1 carbon atom, 2 carbon atoms, 3 carbon atoms, etc., up to and including 20 carbon atoms, although the term "alkyl" also includes instances where no numerical range of carbon atoms is designated).

"Adhesive" as used herein, refers to any substance that adheres or bonds two items together. Implicit in the definition of an "adhesive composition" is the fact that the adhesive is a combination or mixture of more than one species, component or compound, which can include adhesive monomers, oligomers, and/or polymers along with other materials, whereas an "adhesive compound" refers to a single species, such as an adhesive polymer or oligomer.

"Polymer" and "polymer compound" are used interchangeably herein, to refer generally to the combined the products of a single chemical polymerization reaction. Polymers are produced by combining monomer subunits into a covalently bonded chain. Polymers that contain only a single type of monomer are known as "homopolymers", while polymers containing a mixture of monomers are known as "copolymers." It is well known in the art that copolymers synthesized by chemical methods include, but are not limited to, molecules with the following types of monomer arrangements:

alternating copolymers, which contain regularly alternating monomer residues;

periodic copolymers, which have monomer residue types arranged in a repeating sequence;

random copolymers, which have a random sequence of monomer residue types statistical copolymers, which have monomer residues arranged according to a known statistical rule; and block copolymers, which have two or more homopolymer subunits linked by covalent bonds.

The blocks of homopolymer within block copolymers, for example, can be of any length and can be blocks of uniform or variable length. Block copolymers with two or three distinct blocks are called diblock copolymers and triblock copolymers, respectively.

The skilled artisan will appreciate that a single copolymer molecule may have different regions along its length that can be characterized as an alternating, periodic, random, etc., while a copolymer product of a chemical polymerization reaction may contain individual molecules that each differ in the arrangement of monomer units. The skilled artisan will further be knowledgeable in methods for synthesizing each of these types of copolymers, and for varying reaction conditions to favor one type over another.

Furthermore, the length of a "polymer" according to the present invention, will typically vary over a range or average size produced by a particular reaction. The skilled artisan will be aware, for example, of methods for controlling the average length of a polymer produced in a given reaction and also of methods for size-selecting polymers after they have been synthesized.

Unless a more restrictive term is used, polymer is intended to encompass homopolymers, and copolymers having any arrangement of monomer subunits as well as copolymers containing individual molecules having more than one arrangement. With respect to length, unless otherwise indicated, any length limitations recited for the polymers described herein are to be considered averages of the lengths of the individual molecules in polymer.

As used herein, "oligomer" or "oligomeric" refers to a polymer having a finite number of repeating monomers structural units. Oligomers of the invention typically have 2 to about 100 repeating monomer units; frequently 2 to about 30 repeating monomer units; and often 2 to about 10 repeating monomer units; and usually have a molecular weight up to about 3,000.

The skilled artisan will appreciate that oligomers and polymers may, depending on the availability of polymerizable groups or side chains, subsequently be incorporated as monomers in further polymerization or crosslinking reactions.

"Modulus" or "Young's modulus" as used herein, is a measure of the stiffness of a material. Within the limits of elasticity, modulus is the ratio of the linear stress to the linear strain which can be determined from the slope of a stress-strain curve created during tensile testing.

"Thixotropy" as used herein, refers to the property of a material which enables it to stiffen or thicken in a relatively short time upon standing, but upon agitation or manipulation to change to low-viscosity fluid; the longer the fluid undergoes shear stress, the lower its viscosity. Thixotropic materials are therefore gel-like at rest but fluid when agitated and have high static shear strength and low dynamic shear strength, at the same time.

As used herein, "aliphatic" refers to any alkyl, alkenyl, or cycloalkyl moiety.

As used herein, "alkyl" refers to straight or branched chain hydrocarbyl groups having from 1 up to about 500 carbon atoms. Whenever it appears herein, a numerical range, such as "1 to 500" or "$C_1$-$C_{500}$", refers to each integer in the given range; e.g., "$C_1$-$C_{500}$ alkyl" means that an alkyl group may comprise only 1 carbon atom, 2 carbon atoms, 3 carbon atoms, etc., up to and including 500 carbon atoms, although the term "alkyl" also includes instances where no numerical range of carbon atoms is designated. "Substituted alkyl" refers to alkyl moieties bearing substituents that include but are not limited to alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, amido, —C(O)H, —C(O)O—, —C(O)—, —S—, —S(O)$_2$—, —OC(O)—O—, —NR—C(O)—, —NR—C(O)—NR—, —OC(O)—NR—, wherein R is H or lower alkyl, acyl, oxyacyl, carboxyl, carbamate, sulfonyl, sulfonamide, and sulfuryl.

As used herein, "cycloalkyl" refers to saturated, cyclic ring-containing groups containing in the range of about 3 up to about 20 carbon atoms. In certain embodiments, cycloalkyl groups have in the range of about 4 up to about 12 carbon atoms, and in yet further embodiments, cycloalkyl groups have in the range of 5 up to about 8 carbon atoms. "Substituted cycloalkyl" refers to cycloalkyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "hetero" refers to groups or moieties containing one or more heteroatoms such as N, O, and S. Thus, for example "heterocyclic" refers to cyclic (i.e., ring-containing) groups having e.g. N, O, or S as part of the ring structure. "Heteroaryl" and "heteroalkyl" moieties are aryl and alkyl groups, respectively, containing e.g. N, O, or S as part of their structure. Hetero-containing groups may also be substituted. For example, "substituted heterocyclic" refers to a ring-containing group having in the range of 3 up to 14 carbon atoms that contains one or more heteroatoms and also bears one or more substituents, as set forth above.

As used herein, "alkenyl" refers to straight or branched chain hydrocarbyl groups having at least one carbon-carbon double bond, and having in the range of about 2 up to 100 carbon atoms, and "substituted alkenyl" refers to alkenyl groups further bearing one or more substituents as set forth above.

As used herein, "alkylene" refers to a divalent alkyl moiety, and "oxyalkylene" refers to an alkylene moiety containing at least one oxygen atom instead of a methylene ($CH_2$) unit.

"Substituted alkylene" and "substituted oxyalkylene" refer to alkylene and oxyalkylene groups further bearing one or more substituents as set forth above.

As used herein, the term "phenol" includes compounds having one or more phenolic functions per molecule. The terms aliphatic, cycloaliphatic and aromatic when used to describe phenols refers to phenols to which aliphatic, cycloaliphatic and aromatic residues or combinations of these backbones are attached by direct bonding or ring fusion.

As used herein, an "alkene" or "olefin" refers to an unsaturated compound containing at least one carbon-to-carbon double bond.

"Allyl" as used herein, refers to refers to a compound bearing at least one moiety having the structure:

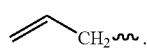

"Imide" as used herein, refers to a functional group having two carbonyl groups bound to a primary amine or ammonia. The general formula of an imide of the invention is:

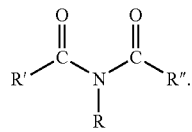

"Polyimides" are polymers of imide-containing monomers. Polyimides typically have one of two forms: linear or cyclic. Non-limiting examples of linear and cyclic (e.g. an aromatic heterocyclic polyimide) polyimides are shown below for illustrative purposes.

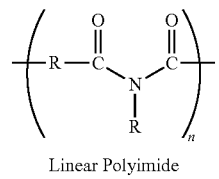

Linear Polyimide

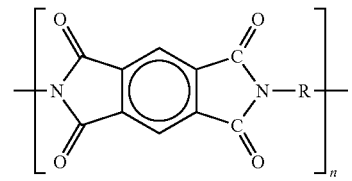

Aromatic Heterocyclic Polyimide

"Maleimide," as used herein, refers to an N-substituted maleimide having the formula as shown below:

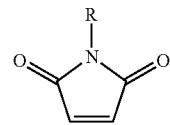

where R is an aromatic, herteroaromatic, aliphatic, or polymeric moiety.

"Bismaleimide" or "BMI", as used herein, refers to a polyimide having the general structure shown below:

where R is an aromatic, herteroaromatic, aliphatic, or polymeric moiety.

As used herein, the term "acrylate" refers to a compound bearing at least one moiety having the structure:

[structure: acrylate]

As used herein, the term "acrylamide" refers to a compound bearing at least one moiety having the structure:

[structure: acrylamide]

As used herein, the term "methacrylate" refers to a compound bearing at least one moiety having the structure:

[structure: methacrylate]

As used herein, the term "methacrylamide" refers to a compound bearing at least one moiety having the structure:

[structure: methacrylamide]

As used herein "epoxy" refers to a thermosetting epoxide polymer that cures by polymerization and crosslinking in the presence of a catalyst to form a polyether thermoset or when mixed with a co-curative compound or "hardener," also referred to as a "curing agent" or "curative." Epoxies of the present invention include, but are not limited to aliphatic, cycloaliphatic, glycidyl ether, glycidyl ester, glycidyl amine epoxies, and the like, and combinations thereof. Epoxies of the invention include compounds bearing at least one moiety having the structure:

[structure: epoxide]

As used herein, the term "oxetane" refers to a compound bearing at least one moiety having the structure:

[structure: oxetane]

Itaconate, as used herein refers to a compound bearing at least one moiety having the structure:

[structure: itaconate]

As used herein, "siloxane" refers to any compound containing a Si—O moiety. In certain embodiments, siloxanes of the invention include 2 or more repeating units of Si—O.

As used herein, the term "vinyl ether" refers to a compound bearing at least one moiety having the structure:

[structure: vinyl ether]

As used herein, the term "vinyl ester" refers to a compound bearing at least one moiety having the structure:

[structure: vinyl ester]

As used herein, "styrenic" refers to a compound bearing at least one moiety having the structure:

[structure: styrenic]

"Oxazoline" as used herein, refers to a compound bearing at least one moiety having the structure:

[structure: oxazoline]

"Benzoxazine" as used herein, refers to a compound bearing at least one moiety having the structure:

[structure: benzoxazine]

"Fumarate" as used herein, refers to a compound bearing at least one moiety having the structure:

[structure: fumarate]

"Propargyl" as used herein, refers to a compound bearing at least one moiety having the structure:

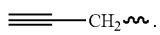

"Cyanate" as used herein, refers to a compound bearing at least one moiety having the structure:

As used herein, "norbornyl" refers to a compound bearing at least one moiety having the structure:

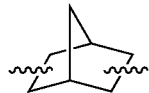

"Diamine," as used herein, refers generally to a compound or mixture of compounds, where each species has 2 amine groups.

A "diol" according to the present invention, is a compound containing two hydroxyl groups (—OH groups); while "polyol" refers to alcohols containing multiple hydroxyl groups.

"Thermoplastic," as used herein, refers to the ability of a compound, composition or other material (e.g. a plastic) to melt to a liquid when heated and freeze to solid, often brittle and glassy, state when cooled sufficiently.

"Thermoset," as used herein, refers to the ability of a compound, composition or other material to irreversibly "cure" to a stronger, harder form. Thermoset materials are typically polymers that may be cured, for example, through heat (e.g. above 200 degrees Celsius, or in the presence of appropriate catalysts at lower temperatures), via a chemical reaction (e.g. epoxy), or through irradiation (e.g. U.V. irradiation).

Thermoset materials, such as thermoset polymers or resins, are typically liquid or malleable forms prior to curing, and therefore may be molded or shaped into their final form, and/or used as adhesives. Curing transforms the thermoset resin into an infusible solid or rubber by a cross-linking process. Thus, energy and/or catalysts are added that cause the molecular chains to react at chemically active sites (unsaturated or epoxy sites, for example), linking the polymer chains into a rigid, 3-D structure.

The invention is based on the discovery that a certain polyether oligomers are useful as adhesives for the microelectronic packaging industry. When incorporated into adhesive compositions, the polyether oligomers of the invention provide increased conductivity, hydrophobicity, lower modulus, lower viscosity, and hydrolytic stability.

Furthermore, an unexpected but useful property of certain invention oligomers is that they offer significantly higher electrical conductivity in silver-filled formulations as compared to other thermoset resins. The relatively low viscosity of many of the polyether oligomers of the invention also permits higher filler loading, which further enhances the benefit to conductivity performance (both electrical and thermal).

The polyether backbones of thermosets based on the oligomers of the invention are impervious to hydrolysis in alkaline environments and are resistant to hydrolysis in all but the most strongly acidic environments. The invention oligomers, furthermore, have good resistance to degradation in hot, moist conditions.

The oligomers described herein are broadly useful as thermoset resins, coatings and adhesives. The oligomers of the invention are therefore valuable in a variety of applications in addition to the microelectronic packaging industry. Invention oligomers can be used, for example, in automotive, marine, and aerospace coatings and adhesives. The properties of certain invention oligomers make them suitable for use in dental matrix resins and adhesives. Invention oligomers can also be used as components of matrix resins for composites used in sports equipment, automotive bodies, and boat construction. The oligomers of the invention also have attractive properties for use in diverse industrial applications such as thread-lock materials and building materials.

The invention is based on the discovery that certain polyether oligomers are useful as adhesives for the microelectonic packaging industry. Thus, present invention provides oligomers that can be represented by structural formula I:

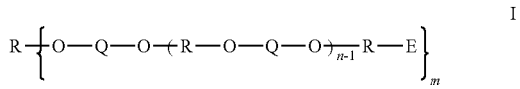

where R and Q are each independently substituted or unsubstituted aliphatic, aryl, or heteroaryl; m is 1 to 4; n is 1 to about 10; and each E is independently acrylate, methacrylate, maleimide, styrenic, vinyl ester, olefin, allyl, vinyl ether, itaconate, fumarate, epoxy, oxetane, oxazoline, benzoxazine, cyanate ester, or propargyl ether.

In certain embodiments, each E is an acrylate, methacrylate, maleimide or styrenic. In yet further embodiments, each E is independently acrylate or methacrylate.

In certain embodiments, R is a substituted or unsubstituted cycloalkyl having from 3 to about 30 carbon atoms. In particular embodiments, R is a substituted or unsubstituted cycloalkyl having from 5 to about 15 carbon atoms. In yet further embodiments, substituted or unsubstituted cycloalkyl having from 6 to about 12 carbon atoms. R can for example, be an unsubstituted $C_4$-$C_{20}$, $C_5$-$C_{15}$ or $C_6$ to $C_{12}$ cycloalkyl. In some embodiments, R is a substituted or unsubstituted cyclopentyl, cyclohexyl, norbornyl, tetracyclododecyl, or dicyclopentadienyl.

A wide variety of aryl and heteroaryl moieties are contemplated for Q in the practice of the invention. In certain embodiments, Q is a substituted or unsubstituted aryl or heteroaryl having from 6 to about 20 carbon atoms. In particular embodiments, Q is $C_6$-$C_{14}$, or a $C_6$-$C_{12}$ substituted or unsubstituted aryl. In other embodiments, Q is phenyl or naphthyl. In further embodiments, Q is a $C_3$-$C_{30}$, $C_4$-$C_{20}$, $C_5$-$C_{15}$ or $C_6$ to $C_{12}$ substituted or unsubstituted cycloalkyl, such as $C_4$-$C_{20}$, $C_5$-$C_{15}$ or $C_6$ to $C_{12}$ substituted or unsubstituted cycloalkyl. For example, Q can be norbornyl. In yet another embodiment, Q is a $C_1$-$C_{50}$, $C_2$-$C_{40}$, or $C_2$ to $C_{36}$ linear or branched, substituted or unsubstituted alkyl chain.

In certain embodiments, the polyether oligomers of the invention have a total oxygen content less than about 20% by weight. In other embodiments, the oxygen content is less than about 15% by weight. In still further embodiments, the combined oxygen and nitrogen content of the polyether oligomers does not exceed 20%, 15% or 10%, by weight of the oligomer molecule.

The oligomers of the invention are readily prepared according to organic chemistry techniques well-known to those skilled in the art. Two methods suitable for use in the practice of the invention include the direct condensation of diol and polyol compounds in the presence of an acid catalyst (i.e. direct etherification), and the Williamson Synthesis (i.e. preparing ethers by reaction of an alkoxide ion with a primary alkyl halide via an $S_N2$ reaction.). The direct etherification can generally only be used where all of the alcohol functional groups in the reaction are primary, but even then the yields may be reduced through elimination as a competing side reaction. The advantage of direct etherification is that the final monomers can be synthesized in same pot without the requirement for a separate work-up step. However, the single pot synthesis is limited to circumstances where the end-capping functional group is itself attached via an acid catalyzed reaction.

Polyether oligomers of the invention include those represented by structural formula II:

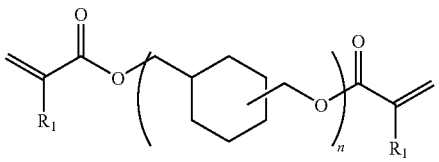

II where $R_1$ is H or Me; and n is 1-10.

Polyether compounds according to the invention also include those represented by structural formula III:

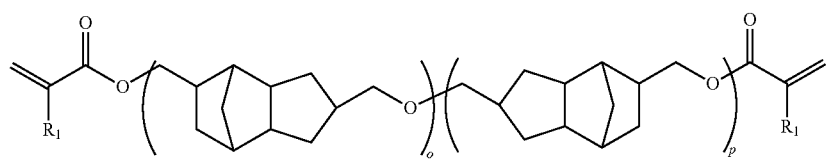

III where $R_1$ is H or Me, and (o+p) is 1-10. In certain embodiments of formula III, each o and p is independently 1-5. In yet further embodiments, (o+p) is 2-5.

The oligomers represented by structures II and III can be prepared via the condensation of individual diol compounds to form a di-hydroxyl functional polyether backbone. The resulting oligomeric diols are then converted to the final functional oligomers through condensation with acrylic and methacrylic acids.

A more complex range of oligomers can obtained when two or more different diols or polyols are used to prepare the polyether backbone. Those skilled in the art will recognize that a complex assortment of oligomer molecules results from the condensation of a mixture of two or more diols and/or polyols based on a statistical distribution of the starting materials. Exemplary oligomers of the invention synthesized from mixed diols and/or polyols are set forth below:

COMPOUND 1

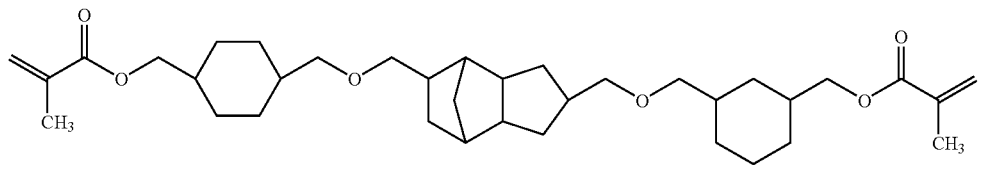

Compound 1a

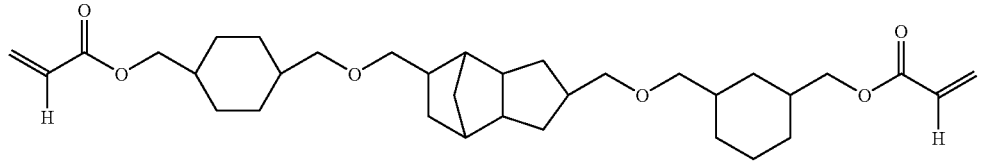

Compound 1b

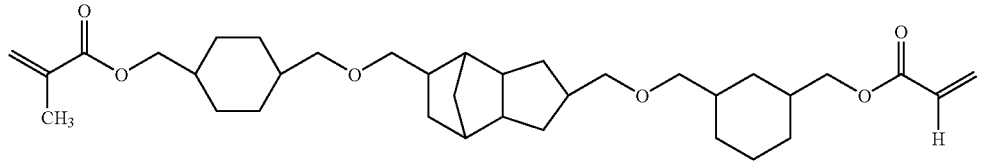

Compound 1c

-continued
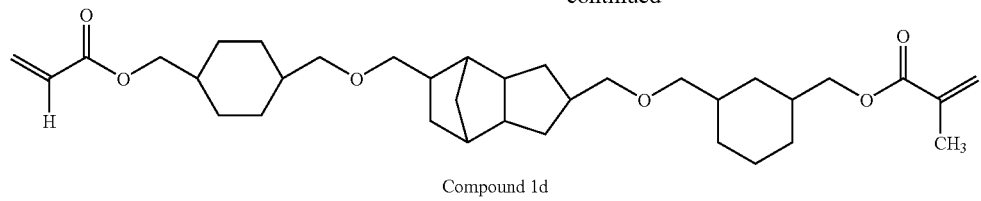
Compound 1d
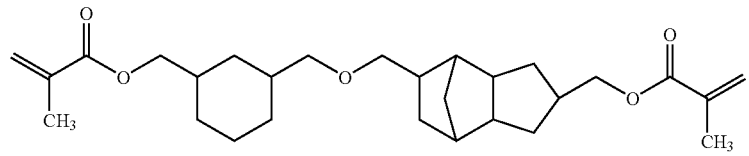
Compound 2a
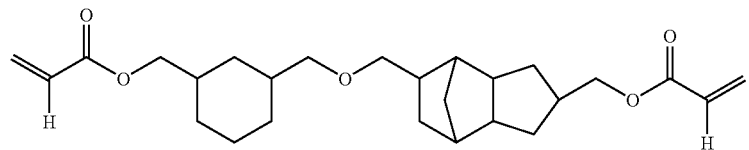
Compound 2b
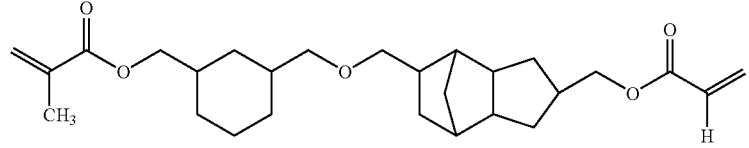
Compound 2c
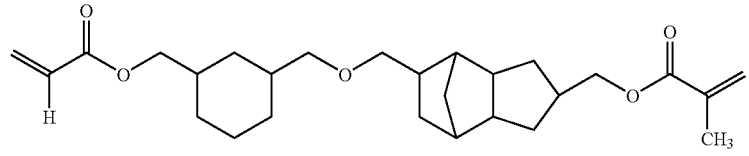
Compound 2d
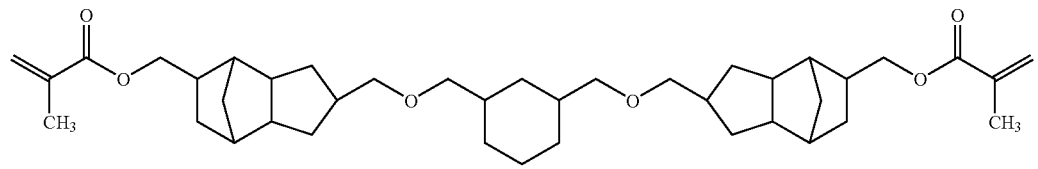
Compound 3a
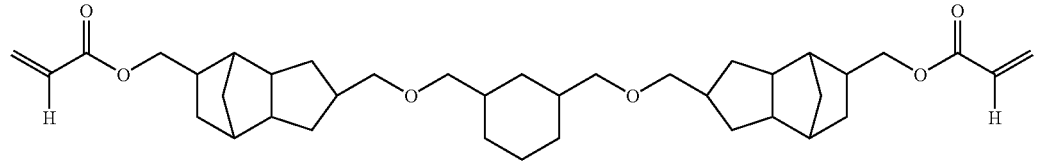
Compound 3b
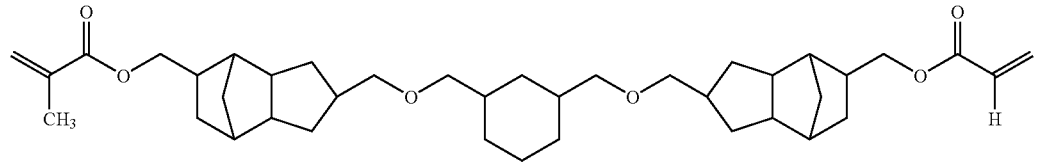
Compound 3c
COMPOUND 2
COMPOUND 3

-continued
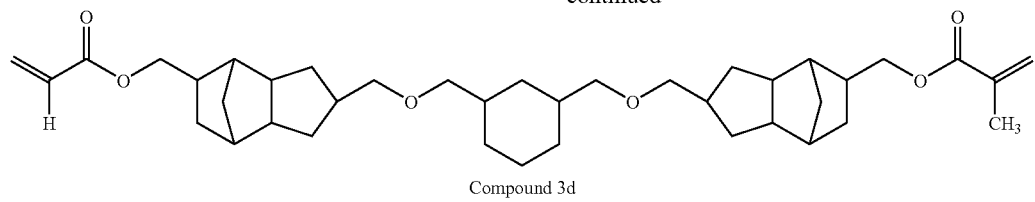
Compound 3d
COMPOUND 4
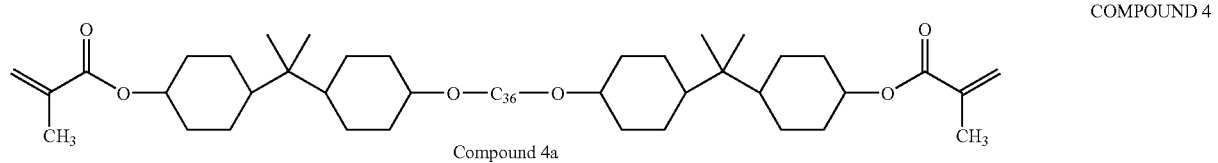
Compound 4a
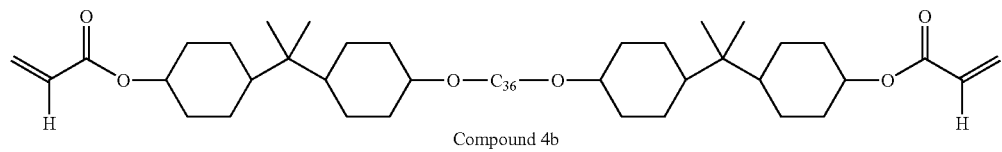
Compound 4b
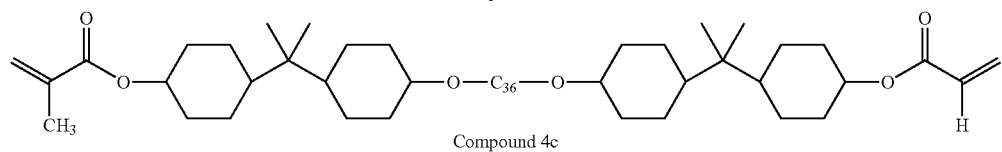
Compound 4c
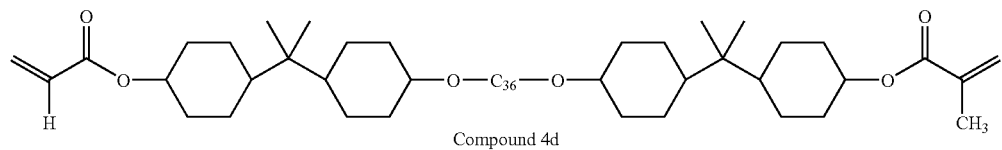
Compound 4d
COMPOUND 5
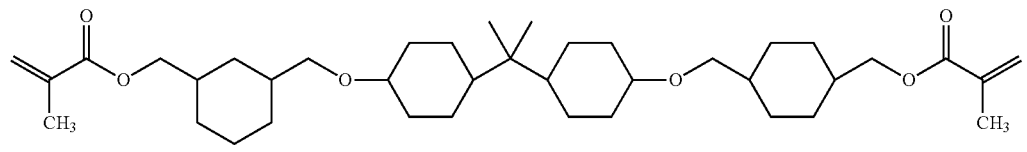
Compound 5a
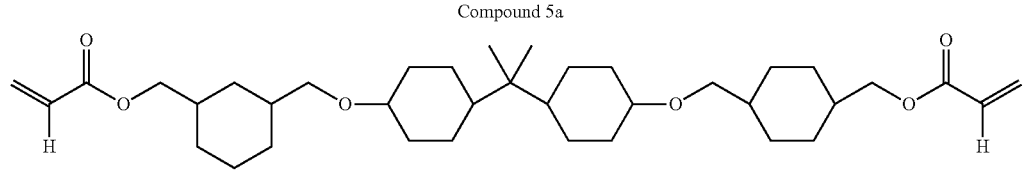
Compound 5b
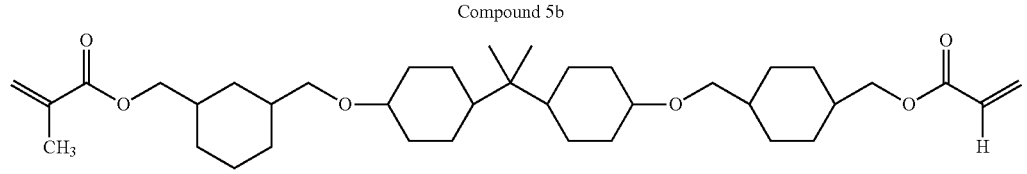
Compound 5c
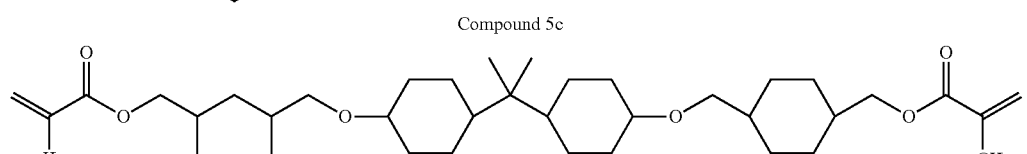
Compound 5d COMPOUND 6
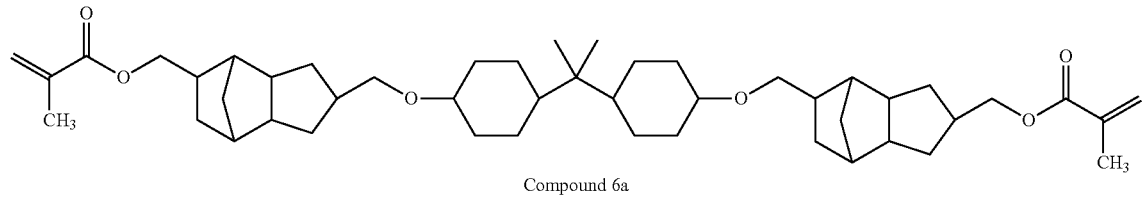
Compound 6a
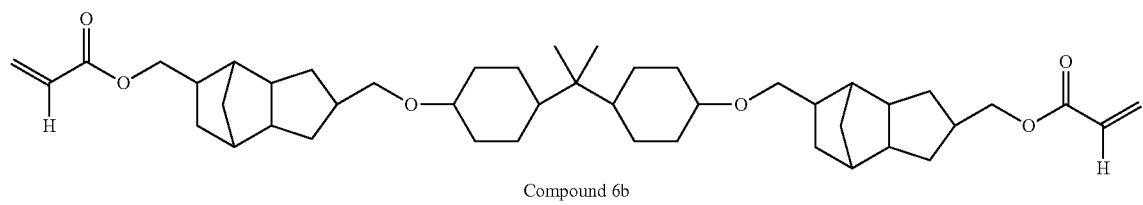
Compound 6b
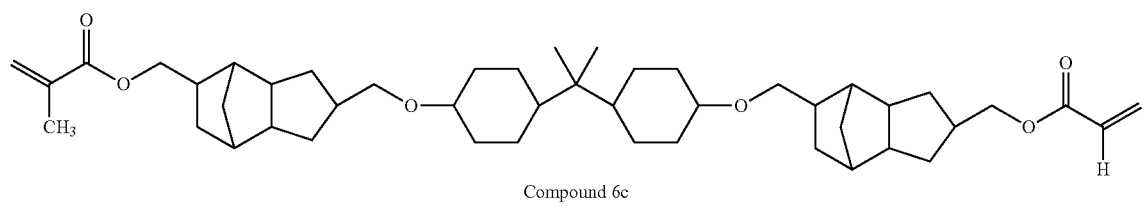
Compound 6c
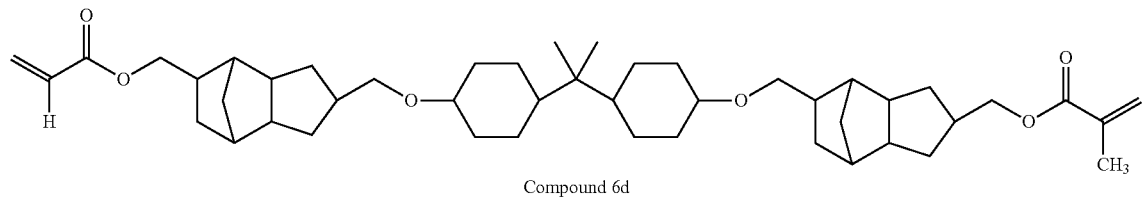
Compound 6d
COMPOUND 7
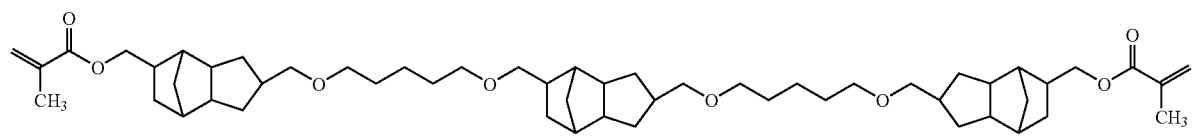
Compound 7a
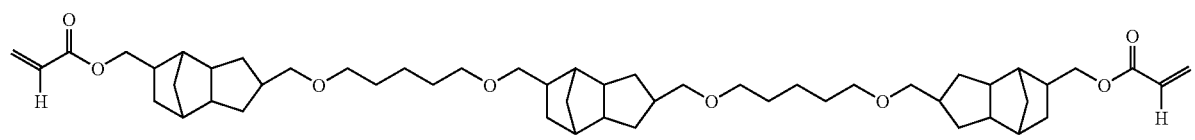
Compound 7b
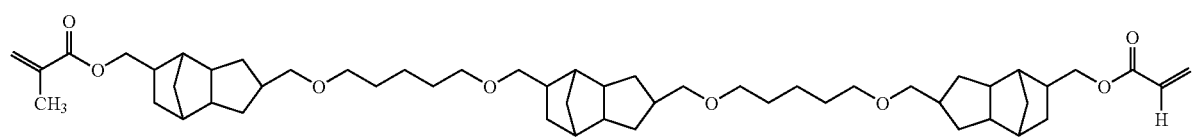
Compound 7c
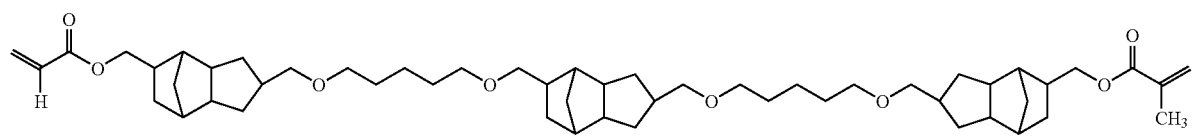
Compound 7d COMPOUND 8
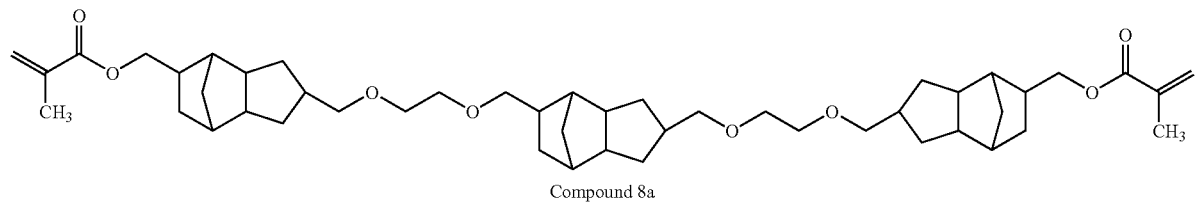
Compound 8a
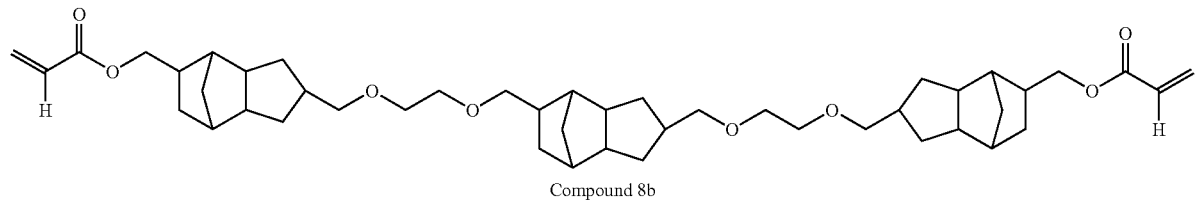
Compound 8b
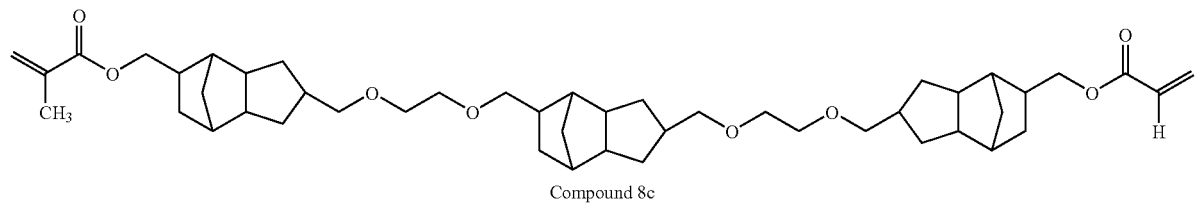
Compound 8c
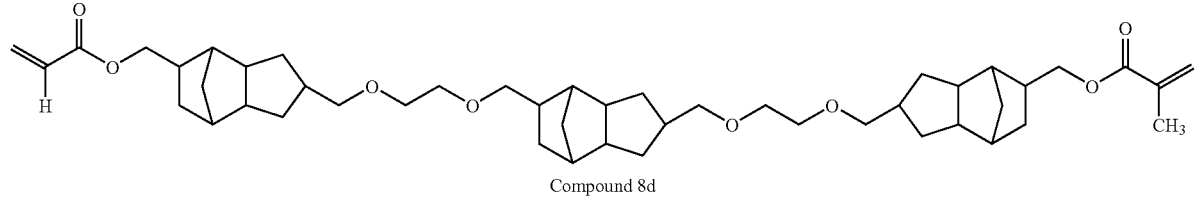
Compound 8d
COMPOUND 9
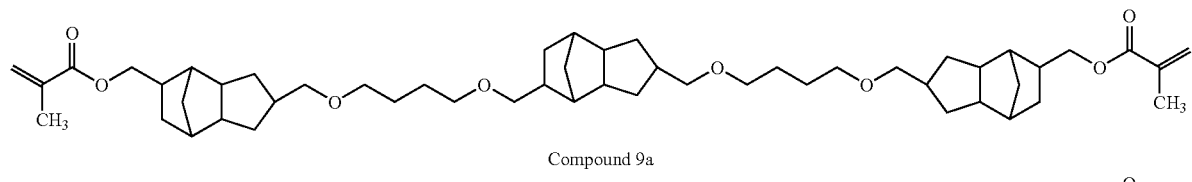
Compound 9a
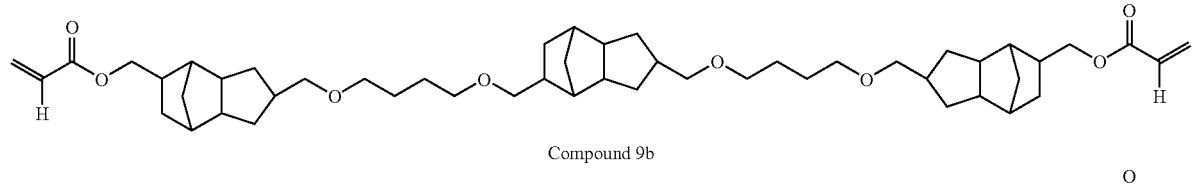
Compound 9b
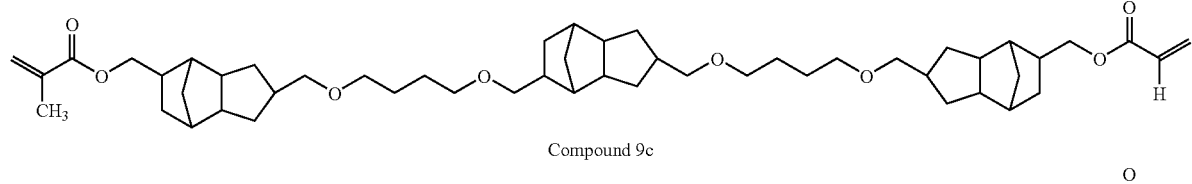
Compound 9c
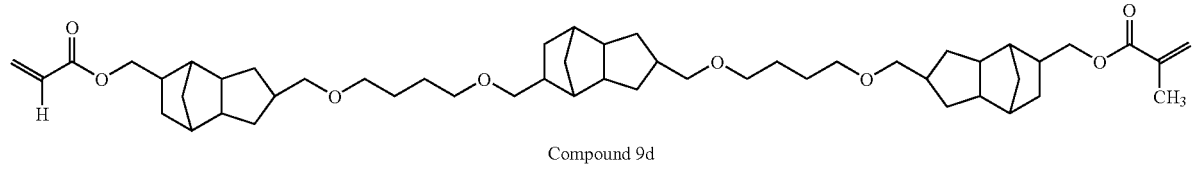
Compound 9d Also provided by the invention are oligomers represented by the structural formula IV:

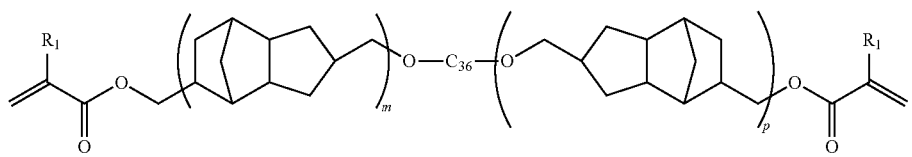

where each $R_1$ is independently H or Me; m and p are each independently 1 to 10; and $C_{36}$ represents a dimer diol residue. Dimer diol is a $C_{36}$ difunctional polyol formed by hydrogenation of the $C_{36}$ dimer acid. In certain embodiments of formula IV, m and p are each independently 1-5. In other embodiments, (m+p) is 2-5.

Adhesive Compositions Containing Polyether Oligomers

The polyether oligomers of the invention may be used independently as adhesives or combined with other materials and reagents to prepare adhesive compositions. In certain embodiments, the polyether oligomers may be combined with other adhesives and/or resins to prepare adhesive compositions. A polyether oligomer of the invention may be used as the sole thermoset of an adhesive composition of the invention. In other embodiments, the polyether oligomer of the invention may be combined with other thermoset to make a fully formulated adhesive composition.

In certain embodiments, the polyether oligomer is present in an adhesive composition in an amount from 0.5 weight percent (wt %) to about 98 wt %, based on the total weight of the composition. In another embodiment, is the adhesive composition includes at least one co-monomer, which is typically present in an amount from 10 wt % to about 90 wt %, based on the total weight of the composition. Co-monomers suitable for use in the adhesive compositions include, but are not limited to, acrylates, methacrylates, maleimides, vinyl ethers, vinyl esters, styrenic compounds, allyl functional compounds, and olefins.

In one embodiment, the present invention provides adhesive compositions including at least one polyether oligomer of the invention and at least one curing initiator.

Curing Initiators. The curing initiator is typically present in adhesive compositions of the invention at an amount from 0.1 wt % to about 5 wt %, based on total weight of the composition, and is typically a free-radical initiator. As used herein, the term "free radical initiator" refers to any chemical species, which, upon exposure to sufficient energy (e.g., light or heat,), decomposes into two parts which are uncharged, but which each posses at least one unpaired electron. Free radical initiators contemplated for use in the practice of the present invention are compounds which decompose (i.e., have a half life in the range of about 10 hours) at temperatures in the range of about 70° C. up to 180° C. Exemplary free radical initiators contemplated for use in the practice of the present invention include peroxides (e.g., dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, and tert-butyl hydroperoxide), azo compounds (e.g., 2,2'-azobis(2-methyl-propanenitrile), 2,2'-azobis(2-methylbutanenitrile), and 1,1'-azobis(cyclohexanecarbonitrile)), and other free-radical initiators that will be well-known in the art.

Photoinitiators. Free radical initiators also include photoinitiators. For invention adhesive compositions that contain a photoinitiator, the curing process can be initiated, for example, by UV radiation. In one embodiment, the photoinitiator is present at a concentration of 0.1 wt % to 5 wt %, based on the total weight of the organic compounds in the composition (excluding any filler). In one embodiment, the photoinitiator comprises 0.1 wt % to 3.0 wt %, based on the total weight of the organic compounds in the composition. Photoinitiators include benzoin derivatives, benzilketals, α,α-dialkoxyacetophenones, α-hydroxyalkylphenones, α-aminoalkylphenones, acylphosphine oxides, titanocene compounds, combinations of benzophenones and amines or Michler's ketone, and the like.

In some embodiments, both photoinitiation and thermal initiation may be desirable. For example, curing of a photoinitiator-containing adhesive can be started by UV irradiation, and in a later processing step, curing can be completed by the application of heat to accomplish a free-radical cure. Both UV and thermal initiators may therefore be added to the adhesive compositions of the invention.

In certain embodiments, the invention provides adhesive compositions including 0.5 wt % to about 98 wt % of at least one polyether oligomer described herein, based on total weight of the composition; optionally, 10 wt % to about 90 wt % of at least one co-monomer selected from acrylates, methacrylates, maleimides, vinyl ethers, vinyl esters, styrenic compounds, allyl functional compounds, and olefins, based on total weight of the composition; 0 to about 90 wt % of a conductive filler; 0.1 wt % to about 5 wt % of at least one curing initiator, based on total weight of the composition; and 0.1 wt % to about 4 wt %, of at least one coupling agent, based on total weight of the composition.

Additional Co-Curing Compounds. In certain aspects, the adhesive compositions of the invention include at least one additional compound that can co-cure with the polyether oligomers. The additional compound is typically present in the adhesive compositions from about 10 wt % to about 90 wt % based on total weight of the composition. Such compounds include, for example, epoxies (e.g. epoxies based on glydicyl ethers of alcohols, phenols, bisphenols, oligomeric phenolics, phenolic novolacs, cresolic novolacs, acrylates, methacrylates, maleimides, poly-phenol compounds (e.g. poly(4-hydroxystyrene)), anhydrides, dianhydrides, polyanhydrides such as styrene-maleic anhydride co-polymers, imides, carboxylic acids, dithiols, polythiols, phenol functional mono-maleimides, bismaleimides, polymaleimides, mono-itaconates, mono-maleates, mono-fumarates, acrylic acid, methacrylic acid, cyanate esters, vinyl ethers, vinyl esters, or phenol functional esters, ureas, amides, polyolefins (e.g. amine, carboxylic acid, hydroxy, and epoxy functional) siloxanes (e.g. epoxy, phenolic, carboxylic acid, or thiol functional), cyanoacrylates, allyl functional compounds and styrenic, as well as combinations thereof.

Adhesive Paste Compositions Containing Polyether Oligomers

In certain embodiments, the present invention provides adhesives that are of various consistencies including, liquids, gels, pastes and solids. In one embodiment, the adhesive composition is a paste suitable for attaching an electronics die to a substrate (i.e., die-attach pastes).

In one embodiment, the present invention provides an adhesive composition that include 0.5 wt % to about 98 wt % based on total weight of the composition, of a polyether oligomer represented by structural formula I; 0 to about 90 wt % of a filler, based on total weight of the composition; 0.1 wt % to about 5 wt % of at least one curing initiator, based on total weight of the composition; and 0.1 wt % to about 4 wt %, of at least one coupling agent, based on total weight of the composition.

Coupling Agents. As used herein, the term "coupling agent" refers to chemical species that are capable of bonding to a mineral surface and which also contain polymerizably reactive functional group(s) so as to enable interaction with the adhesive composition, such as a die-attach paste. Coupling agents thus facilitate linkage of the adhesive composition to the substrate to which it is applied.

Exemplary coupling agents contemplated for use in the practice of the present invention include silicate esters, metal acrylate salts (e.g., aluminum methacrylate), titanates (e.g., titanium methacryloxyethylacetoacetate triisopropoxide), zirconates, or compounds that contain a copolymerizable group and a chelating ligand (e.g., phosphine, mercaptan, acetoacetate, and the like). In some embodiments, the coupling agent contains both a co-polymerizable function (e.g., vinyl, acrylate, methacrylate, epoxy, thiol, anhydride, isocyanate, and phenol moieties) and a silicate ester function. The silicate ester portion of the coupling agent is capable of condensing with metal hydroxides present on the mineral surface of substrate, while the co-polymerizable function is capable of co-polymerizing with the other reactive components of invention adhesive compositions, such as die-attach pastes. In certain embodiments coupling agents contemplated for use in the practice of the invention are oligomeric silicate coupling agents such as poly(methoxyvinylsiloxane).

B-Stageable Adhesives

In certain embodiments, the adhesive compositions and die attach pastes of the invention are b-stageable. As used herein, "b-stageable" refers to the properties of an adhesive having a first solid phase followed by a tacky rubbery stage at elevated temperature, followed by yet another solid phase at an even higher temperature. The transition from the rubbery stage to the second solid phase is thermosetting. However, prior to that, the thermosetting material behaves similarly to a thermoplastic material. Thus, such adhesives allow for low lamination temperatures while providing high thermal stability.

The b-stageable adhesive can be dispensed onto a die or a substrate by a variety of methods well known to those skilled in the art. In some embodiments, the adhesive is cast from solution using techniques such as spin coating, spray coating, stencil printing, screen printing, and the like. This dual stage cure is especially attractive for applications were it is desirable to apply an adhesive in liquid form, cure the material to a non-tacky thermoplastic state, and then cure this b-staged adhesive in a final heating step to bond two or more parts together. Thus, this dual stage cure method of the invention is particularly attractive for silicon wafer back coatings. The original adhesive mixture can be spin coated onto the back of a silicon wafer. The coating can then be b-staged with heat or light. The coated wafers can then be diced to yield individual microelectronic components, which may be thermally attached directly to a substrate, and/or stacked together. The thermal "tacking step" re-liquifies the adhesive coating and provides a thermoplastic bond between the parts. The final bonding step involves a thermal (or in some cases light-based) cure to cross-link the b-staged adhesive composition. This method of assembly is highly desirable because it is easier to manufacture (especially for stacked die) than a traditional liquid adhesive assembly, and is much less expensive and wasteful compared to film-based adhesive technology.

In certain embodiments, a solvent may be employed in the practice of the invention. For example, when the b-stageable adhesive is spin coated onto a circular wafer, it is desirable to have an even coating throughout the entire wafer, i.e., the solvent or solvent system should have the ability to deliver the same amount of adhesive to each point on the wafer. Thus, the adhesive will be evenly coated throughout, i.e., there will be the same amount of material at the center of the wafer as at the edges. Ideally, the adhesive is "Newtonian", with a thixotropic slope of 1.0. In certain embodiments, the solvent or solvent systems used to dispense the b-stageable adhesive have slopes ranging from 1.0 to about 1.2.

In some instances, the b-stageable adhesive is dispensed onto the backside of a die that has been coated with a polyimide. Thus, the solvent or solvent system used to dispense the b-stageable adhesive should not have any deleterious effects on the polyimide coating. To achieve this goal, in certain embodiments, the solvent system will include a polar solvent in combination with a nonpolar solvent. Typically, the polar solvent is suitable for use with the polyether oligomers in the b-stageable adhesive, and the nonpolar solvent is a non-solvent for the polyether polymer. In addition, the polar solvent typically has a lower boiling point than the non-polar solvent. Without wishing to be to be limited to a particular theory, it is believed that when the adhesive is dispensed and then b-staged, the lower boiling polar solvent escapes first, leaving behind only the nonpolar non-solvent, essentially precipitating the oligomer uniformly and leaving the polyimide film undamaged.

In some embodiments, the solvent or solvent system has a boiling point ranging from about 150° C. up to about 300° C. In some embodiments, the solvent system is a combination of dimethyl phthalate (DMP), NOPAR 13, and terpineol. In other embodiments, the solvent system is a 1:1 (by volume) ratio of terpineol and NOPAR 13.

In general, b-stageable adhesive compositions of the invention will cure within a temperature range of 80-220° C., and curing will be effected within a length of time of less than 1 minute up to about 60 minutes. The b-stageable adhesive composition may be pre-applied onto either a semiconductor die or onto a substrate. As will be understood by those skilled in the art, the time and temperature curing profile for each adhesive composition will vary, and different compositions can be designed to provide the curing profile that will be suited to the particular industrial manufacturing process.

Additional Compounds. In certain embodiments, the adhesive compositions of the invention, such as die-attach pastes, may contain modifiers that lend additional flexibility and toughness to the resultant cured adhesive. Such modifiers may be any thermoset or thermoplastic material having a $T_g$ of 50° C. or less, and typically will be a polymeric material characterized by free rotation about the chemical bonds, the presence of ether groups, and the absence of ring structures. Suitable such modifiers include polyacrylates, poly(butadiene), polyTHF (polymerized tetrahydrofuran, also known as poly(1,4-butanediol)), CTBN (carboxy-terminated butadiene-acrylonitrile) rubber, and polypropylene glycol. When present, toughening compounds may be in an amount up to about 15 percent by weight of polyether oligomer and any other monomer in the adhesive.

Inhibitors for free-radical cure may also be added to the adhesive compositions and die-attach pastes described herein to extend the useful shelf life. Examples of free-radical inhibitors include hindered phenols such as 2,6-di-tert-butyl-4-methylphenol; 2,6-di-tert-butyl-4-methoxyphenol; tert-butyl hydroquinone; tetrakis(methylene(3,5-di-tert-butyl-4-hydroxyhydrocinnamate))benzene; 2,2'-methylenebis(6-tert-butyl-p-cresol); and 1,3,5-trimethyl-2,4,6-tris(3',5'-di-tert-butyl-4-hydroxybenzyl)benzene. Other useful hydrogen-donating antioxidants such as derivatives of p-phenylenediamine and diphenylamine. It is also well know in the art that hydrogen-donating antioxidants may be synergistically combined with quinones and metal deactivators to make a very efficient inhibitor package. Examples of suitable quinones include benzoquinone, 2-tert butyl-1,4-benzoquinone; 2-phenyl-1,4-benzoquinone; naphthoquinone, and 2,5-dichloro-1,4-benzoquinone. Examples of metal deactivators includeN,N'-bis(3,5-di-tert-butyl-4-hydroxyhydrocinnamoyl)hydrazine; oxalyl bis(benzylidenehydrazide); and N-phenyl-N'-(4-toluenesulfonyl)-p-phenylenediamine. Nitroxyl radical compounds such as TEMPO (2,2,6,6-tetramethyl-1-piperidnyloxy, free radical) are also effective as inhibitors at low concentrations. The total amount of antioxidant plus synergists typically falls in the range of 100 to 2000 ppm relative to the weight of total base resin. Other additives, such as adhesion promoters, in types and amounts known in the art, may also be added.

The adhesive compositions, such as die-attach paste adhesives, described herein will generally perform within the commercially acceptable ranges for die attach adhesives. Commercially acceptable values for die shear for the adhesives on a 80×80 $mil^2$ silicon die are in the range of greater than or equal to 1 kg at room temperature, and greater than or equal to 0.5 kg at 260° C. Acceptable values for warpage for a 500×500 $mil^2$ die are in the range of less than or equal to 70 Nm at room temperature.

Fillers. In some embodiments, fillers are contemplated for use in the practice of the present invention, which can be electrically conductive and/or thermally conductive, and/or fillers which act primarily to modify the rheology of the resulting composition. Examples of suitable electrically conductive fillers that can be employed in the practice of the present invention include silver, nickel, copper, aluminum, palladium, gold, graphite, metal-coated graphite (e.g., nickel-coated graphite, copper-coated graphite, and the like), and the like. Examples of suitable thermally conductive fillers that can be employed in the practice of the present invention include graphite, aluminum nitride, silicon carbide, boron nitride, diamond dust, alumina, and the like. Compounds which act primarily to modify rheology include polysiloxanes (such as polydimethyl siloxanes), silica, fumed silica, fumed alumina, fumed titanium dioxide, calcium carbonate and the like.

Assemblies

The present invention also provides assemblies of components adhered together by the above-described adhesive compositions (e.g. b-stageable adhesives and die-attach pastes) of the invention. Thus, for example, assemblies comprising a first article adhered to a second article by a cured aliquot of an adhesive compostion containing at least one polyether oligomer of the invention are provided. Articles contemplated for assembly employing invention compositions include electronic components such as dies, memory devices (e.g. as flash memory devices), ASIC devices, microprocessors, and other microelectronic components. Assemblies also include microelectronic devices, such as copper lead frames, Alloy 42 lead frames, silicon dice, gallium arsenide dice, and germanium dice, that are adhered to a substrate by a cured aliquot of the above-described adhesive compositions.

Additional embodiments of the invention include adhesive bonded structures containing at least one polyether oligomer described herein. Non-limiting examples of the adhesive bonded structures include electronic components bonded to a substrate, and circuit components bonded to printed wire boards. In other embodiments of the invention, articles of manufactures can be comprised substantially of a cured amount of the composition described herein, such as an industrial, marine, automotive, airline, aerospace, sporting goods, medical or dental article. Such articles of manufacture can also include fillers, extenders, pigments and/or reinforcing materials along with the compositions disclosed herein.

Conditions suitable to cure invention die attach paste adhesives include subjecting the above-described assembly to a temperature of less than about 200° C. for about 0.5 up to 2 minutes. This rapid, short duration heating can be accomplished in a variety of ways, e.g., with an in-line heated rail, a belt furnace, or the like. Optionally, the material can be oven cured at 150-220° C.

Methods of Using Containing Polyether Oligomers and Adhesive Compositions

According to the present invention, methods for adhesively attaching a first article to a second article are provided. Such methods can be performed, for example, by a) applying an adhesive composition of the invention to the first article, the second article or both the first and second articles; b) contacting the first article and the second article, where the first article and the second article are separated only by the adhesive composition applied in step a); and c) curing the adhesive composition applied in step a), thereby adhesively attaching the first article to the second article.

In one aspect of this the first and second articles are a semiconductor die and a substrate, respectively. Typically, according to this aspect the adhesive is a die attach paste. The method can include the steps of applying the adhesive composition (e.g. die attach paste) to the substrate, the semiconductor die, or both the substrate and the semiconductor die; b) melting the adhesive composition applied in step a); c) contacting the semiconductor device and the substrate, where the die and substrate are separated only by the adhesive composition applied in step a); and d) curing the adhesive composition applied in step a), thereby adhesively attaching the semiconductor device to the substrate. Applying the adhesive composition can include spin coating, spray coating, stencil printing, screen printing and other methods well known in the art. It is understood that using the compounds and methods of the present invention, it is possible to prepare adhesives having a wide range of cross-link density by the judicious choice and amount of polyether compounds. The greater proportion of polyfunctional compounds reacted, the greater the cross-link density. If thermoplastic properties are desired, the adhesive compositions can be prepared from (or at least contain a higher percentage of) mono-functional compounds to limit the cross-link density. A minor amount of poly-functional compounds can be added to provide some cross-linking and strength to the composition, provided the amount of poly-functional compounds is limited to an amount that does not diminish the desired thermoplastic properties. Within these parameters, the strength and elasticity of individual adhesives can be tailored to a particular end-use application.

"Cross-linking," as used herein, refers to the attachment of two or more oligomer or longer polymer chains by bridges of an element, a molecular group, a compound or another oligomer or polymer. In general, crosslinking of the oligomers of the invention takes place upon heating. As cross-linking density is increased, the properties of a material can be changed from thermoplastic to thermosetting.

In still further embodiments, the invention provided b-stageable type methods for adhesively attaching a semiconductor die to a substrate. Such methods can be performed, for example, by applying an invention adhesive composition to the substrate, the semiconductor device or both the substrate and the semiconductor device; melting the applied adhesive composition applied; (c) contacting the semiconductor device and the substrate, such that the die and substrate are separated only by the applied adhesive composition; and curing the applied adhesive composition, thereby attaching the semiconductor device to the substrate.

Properties of Adhesives Containing Polyether Oligomers

Advantageously, the polyether oligomers of the invention can impart many properties that are desirable in an adhesive. Historically, the large majority of integrated circuits have been mounted on printed circuit boards using lead-based soldering. However, the demand for lead-free materials is increasing year by year, and electrically conductive adhesives are seen as an environmentally-friendly alternative.

To fully replace lead-based solders, adhesives in the microelectronic industry, adhesives must address the need for signal and power distribution, heat dissipation (i.e., cooling) while at the same time having and maintaining high adhesiveness.

Conductive adhesives typically have conductive fillers dispersed in a polymer matrix. The polymer matrix, when cured, provides the mechanical adhesion, but can interfere with conductivity and increase electrical resistance.

Electrical Resistance. A typical thermoset adhesive composition, such as free-radical cured thermosets, may contain acrylate, methacrylate, maleimide or similar monomers. Therefore, a control adhesive composition containing acrylate monomers was compared to an identical adhesive in which polyether oligomers of the invention replaced the acrylates (see Examples 12-17). Compositions containing polyether oligomers according to structural formula II had significantly lower electrical resistance as compared to the control. Specifically, the adhesive compositions of the invention had resistivity of 0.000027-0.000094 Ohm-cm, even after simulated post mold cure conditions, which was only about 25-50% of the resistivity of the control.

Similarly, thermoset adhesive compositions in which polyether compounds of the invention replaced maleimides had lower resistivity as compared to controls (see Examples 18-21)

Accordingly, the present invention provides thermoset adhesive compositions containing polyether oligomers that have lower resistivity when compared control thermosets. Particularly, the adhesive compositions of the invention may have resistivity in the range of about 0.000001 to about 0.0001 Ohm-cm. In certain embodiments, the resistivity is less than about 0.0001 Ohm-cm; less than about 0.00005 Ohm-cm, or less than about 0.00001 Ohm-cm. In certain embodiments, the adhesives have electrical resistance that is 20-25%, 30-35%, 40-45%, or 50-55% of the resistance of a control thermoset adhesive composition.

Thus the present invention provides methods for reducing the electrical resistance of an adhesive composition by replacing all or a portion of the monomer, such as an acrylate monomer, with a polyether oligomer of the invention. In one embodiment, the polyether oligomer can be represented by structural formula I. In certain aspects the polyether oligomer has the structure of formula II.

Also provided by the invention are methods for reducing the resistivity of an adhesive composition by substituting a polyether oligomer according to formula I, for another monomer, such as an acrylate or a maleimide, in the composition.

Viscosity. Replacing acrylate or maleimide monomers in control adhesive compositions with polyether oligomers of the invention also reduced the viscosity of the adhesive compositions. Low viscosity is an important property for thermoset adhesives which allows them to be workable and to be applied mechanically in a high-throughput fashion, such as through syringes, by robots or other automated mechanisms.

The polyether oligomers of the invention reduced the viscosity of adhesive compositions, in some cases by half. Accordingly, the present invention includes methods for reducing the viscosity of an adhesive composition by replacing part or all of a monomer in the composition with at least one polyether oligomer represented by structural formula I, which can, for example be structural formula II. In certain embodiments, the methods of the invention reduce viscosity by at least 10%, at least 20%, at least 30%, at least 40%, at least 50%, or at least 60%, when compared to a control acrylate-based composition.

The invention also provides adhesive compositions that include polyether oligomers as a monomer in the adhesive, having a 5 rpm viscosity of about 5,000 to about 10,000 centipoises. In some embodiments the viscosity is less than about 10,000, less than about 9,000, less than about 8,000, less than about 7,000 or less than about 6,000 centipoises. In certain embodiments, the adhesives have viscosity that is 50%, 55%, 60%, 65%, 70% or 75% of the viscosity of comparable acrylate- or maleimide-based adhesive compositions.

Such lower viscosity adhesive compositions were able to include significantly more silver, for example than comparable adhesive compositions that did not include the polyether oligomers of the invention. Thus, the present invention includes methods for increasing the amount of a conductive metal, such as silver, in an adhesive composition by replacing an acrylate monomer with a polyether oligomer of the invention. Adhesive compositions containing an increased amount of silver and having increased conductivity are also provided.

Thixotropy. Replacing acrylate monomers in control adhesive compositions with polyether oligomers of the invention also increased the thixotropy of the adhesives. Higher thixotropy allows thermoset adhesives to be easily manipulated upon mixing (e.g. under shear force), yet prevents them from dripping and running.

Accordingly, the present invention includes methods for increasing the thixotropy of an adhesive composition by replacing part or all of the monomer with at least one polyether oligomer represented by structural formula I, which can, for example be structural formula II. In certain embodiments, the methods of the invention increase thixotropy by at least about 5%, at least about 10%, least about 15%, least about 20%, or at least about 25%.

The invention also provides adhesive compositions that include polyether oligomers as a monomer in the adhesive, having a thixotropic index (0.5/5 viscosity ration) of at least about 5.0, of at least about 5.8, at least about 6, at least about 6.25 or at least about 6.5.

The invention will now be further described with reference to the following non-limiting examples.

EXAMPLES

Example 1

Preparation of an Oligomer of Structural Formula II

A single-neck, 500 mL flask was charged with 86.52 g (0.6 mole) Unoxol Diol (a blend of 1,4- and 1,3-cyclohexanedimethanol isomers from Dow Chemical), 40 mL heptane and 1.0 g methanesulfonic acid and a magnetic stir bar. A Dean-Stark trap and condenser were attached. This mixture was refluxed for eighteen hours, under an argon blanket, to collect 9.2 mLs water. The mixture was cooled and 200 mL heptane, 16.2 g (0.225 mole) acrylic acid, 19.4 g (0.225 mole) methacrylic acid, and 210 mg hydroquinone were added. The new mixture was stirred under an air sparge for 3.5 hours and another 5.4 mL of water was collected. The flask was then cooled again and the mixture was placed in a sepratory funnel and extracted with five, twenty-five mL portions of deionized water. The heptane phase was then neutralized with 20 g sodium bicarbonate, dried with 12 g magnesium sulfate and then passed over 30 g silica gel. The heptane was removed to obtain 71.2 g (73.5% of theoretical yield) of a clear, yellow, low viscosity, oily liquid. The viscosity (at 5 rpm) of this product was 225 centipoises at 25.0° C. A thermogravimetric analyis (TGA; 10° C. per minute, air purge) run on the neat monomer had 88.4% residual weight at 300° C. The TGA was repeated on the sample following addition of 2% dicumyl peroxide catalyst and the residual weight at 300° C. was 95.6% with a decomposition onset temperature of 388.9° C. Differential scanning calorimetry (DSC) was run on the catalyzed sample and a mono-modal cure exotherm was observed with an onset temperature of 138.2° C., a cure peak at 147.8° C., and a cure energy of 207 joules per gram. An Fourier transform infrared spectroscopy (FTIR) run on this product revealed prominent absorptions at 2922, 2848, 1721, 1637, 1407, 1295, 1181, 1122, 983, and 810 wave numbers. Gel permeation chromatography (GPC) was run on this product and it was found to consist of a mixture of approximately 37.2% mono (n=1), 26.1% di-(n=2), 15.3% tri-(n=3), and 14.1% tetra-(n=4) compounds according to Structure II.

Example 2

Preparation of an Oligomer of Structural Formula II at Controlled Temperature

The procedure of Example 1 was repeated, except that the first (etherification) step was controlled at 160° C. The water collected in the first step was 9.0 mL. The water collected in the second step was 6.2 mL. The recovered product was a clear, light orange, liquid that weighed 72.6 g (75.0% of theoretical yield). The 5 rpm viscosity at 25.0° C. was 264 centipoises. The FTIR trace was virtually identical to that observed in Example 1. The residual weight via TGA for this monomer was 90.2% and 96.9% for the neat and catalyzed (2% dicumyl peroxide) samples at 300° C., respectively. A DSC run on this compound had an onset temperature at 138.6° C., a cure maxima at 148.4° C., and a cure energy of 247.5 joules per gram. A GPC was run on this product and it was found to consist of a mixture of approximately 28.6% mono (n=1), 26.2% di-(n=2), 17.0% tri-(n=3), and 20.1% tetra-(n=4) compounds according to Structure II.

Example 3

Preparation of an Oligomer of Structural Formula II with Increased Catalyst

The procedure of Examples 1 and 2 was repeated, except that the quantity of methanesulfonic acid catalyst was increased from 1.0 to 10.0 grams, and the first (etherification) step was controlled at 145-155° C. The water collected in the first step was 9.2 mL. The water collected in the second step was 7.2 mL. The recovered product was a clear, light orange, liquid that weighed 76.1 g (75.0% of theoretical yield). The 5 rpm viscosity at 25.0° C. was 149 centipoises. The FTIR trace was virtually identical to that of Examples 1 and 2. The residual weight via TGA for this polyether was 79.2% and 93.1% for the neat and catalyzed (2% dicumyl peroxide) samples at 300° C., respectively. A DSC run on the catalyzed compound had an onset temperature at 140.3° C., a cure maxima at 152.1° C., and a cure energy of 270.9 joules per gram. A GPC was run on this product and it was found to consist of a mixture of approximately 40.9% mono (n=1), 25.2% di-(n=2), 14.3% tri-(n=3), and 10.5% tetra-(n=4) compounds according to Structure II.

Example 4

Preparation of an Oligomer of Structural Formula III

A two-neck, 500 mL flask was charged with 117.6 g (0.60 mole) tricyclodecane dimethanol, 40 mL heptane, and 10.0 g methanesulfonic acid. This mixture was refluxed for seventy minutes at 145° C. (although there was an initial spike up to 176° C.) to collect 10.1 mL of water. The mixture had turned dark purple at first and then turned to a black-green color as the reaction proceeded. The mixture was cooled and 16.2 g (0.225 mole) acrylic acid, 19.4 g (0.225 mole) methacrylic acid, 200 mL heptane, and 210 mg hydroquinone were added. The new mixture was refluxed under an air sparge for 90 minutes and 7.3 mLs water was collected. The mixture was worked up as described above in Example 1 to yield 116.2 g of a clear, dark red, viscous liquid. The 5 rpm viscosity of this product was 7,376 centipoises at 25.0° C. A TGA (10° C. per minute, air purge) run on the neat monomer had 85.9% residual weight at 300° C. The TGA was repeated on the sample with 2% added dicumyl peroxide catalyst and the residual weight at 300° C. was 94.9% with a decomposition onset temperature of 377.6° C. A DSC was run on the catalyzed sample and a mono-modal cure exotherm was observed with an onset temperature of 134.6° C., a cure peak at 150.6° C., and a cure energy of 182 joules per gram. An FTIR run on this product had prominent absorptions at 2946, 1721, 1637, 1451, 1294, 1162, 1105, 982, and 810 wave numbers. A GPC was run on this product and it was found to consist of a mixture of approximately 32.2% mono (n=1), 21.0% di-(n=2), 20.3% tri-(n=3), and 10.8% tetra-(n=4) compounds according to Structure III.

Example 5

Preparation of an Oligomer of Structural Formula Iv

A two-neck, 500 mL flask was charged with 94.1 g (0.48 mole) tricyclodecanedimethanol, 64.3 g (0.12 mole) dimer-diol, 40 mL heptane, and 5.0 g methanesulfonic acid. This mixture was refluxed under an argon blanket at 140-150° C. to obtain 9.6 ml water. The mix was cooled and 16.2 acrylic acid, 19.4 g methacrylic acid, and 210 mg hydroquinone were added. This mixture was then refluxed for 2.5 hours under an air sparge to obtain 5.2 mL water. The product was worked up as in the previous examples to obtain 153.6 g of a clear, viscous, red-brown liquid. A TGA (10° C. per minute, air purge) run on the neat monomer had 97.2% residual weight at 300° C. The TGA was repeated on the sample with 2% added dicumyl peroxide catalyst and the residual weight at 300° C. was 97.5% with a decomposition onset temperature of 423.1° C. A DSC was run on the catalyzed sample and a mono-modal cure exotherm was observed with an onset temperature of 137.2° C., a cure peak at 150.2° C., and a cure energy of 96.8 joules per gram. An FTIR run on this product had prominent absorptions at 2929, 2853, 1725, 1637, 1462, 1405, 1294, 1185, 1109, 1055, 983, and 810 wave numbers.

Example 6

Preparation of Compound 1

A two-neck, 500 mL flask was charged with 57.68 g (0.40 mole) Unoxol Diol, 39.2 g (0.20 mole) tricyclclodecanediol, 3.0 g sulfuric acid, and 40 mL heptane. This mixture was refluxed under an argon blanket at 145° C. to collect 8.2 mL water. The mixture was cooled and 16.2 g acrylic acid, 19.4 g methacrylic acid, 200 mL heptane and 210 mg hydroquinone. The new mixture was refluxed under an air sparge for three hours to collect 7.8 mL of water. The usual work up provided 84.9 g of a fairly mobile, clear, brown liquid. The 5 rpm viscosity of this product was 476 centipoises at 25.0° C. A TGA (10° C. per minute, air purge) run on the neat monomer had 90.5% residual weight at 300° C. The TGA was repeated on the sample with 2% added dicumyl peroxide catalyst and the residual weight at 300° C. was 97.0% with a decomposition onset temperature of 428.9° C. A DSC was run on the catalyzed sample and a mono-modal cure exotherm was observed with an onset temperature of 137.6° C., a cure peak at 145.6° C., and a cure energy of 189.7 joules per gram. An FTIR run on this product had prominent absorptions at 2930, 2855, 1721, 1637, 1406, 1295, 1167, 983, and 810 wave numbers. Thermomechanical analylsis (TMA) was performed on a cured sample of this monomer. It was found to have a glass transition ($T_g$) of 49.7° C., an $\alpha_1$=54.2 ppm/° C., and an $\alpha_2$=173.4 ppm/° C.

Example 7

Preparation of Compound 2

A two-neck, 500 mL flask was charged with 43.26 g (0.30 mole) Unoxol Diol, 58.8 g (0.30 mole) tricyclclodecanediol, 3.0 g sulfuric acid, and 40 mL heptane. This mixture was refluxed under an argon blanket at 145° C. to collect 9.2 mL water. The mixture was cooled and 16.2 g acrylic acid, 19.4 g methacrylic acid, 200 mL heptane and 210 mg hydroquinone. The new mixture was refluxed under an air sparge for three hours to collect 6.6 mL of water. The usual work up provided 94.4 g of a moderately viscous, clear, brown liquid. The 5 rpm viscosity of this product was 1186 centipoise at 25.0° C. A TGA (10° C. per minute, air purge) run on the neat monomer had 93.6% residual weight at 300° C. The TGA was repeated on the sample with 2% added dicumyl peroxide catalyst and the residual weight at 300° C. was 95.4% with a decomposition onset temperature of 426.3° C. A DSC was run on the catalyzed sample and a mono-modal cure exotherm was observed with an onset temperature of 133.8° C., a cure peak at 145.6° C., and a cure energy of 208.7 joules per gram. An FTIR run on this product had prominent absorptions at 2938, 2858, 1721, 1637, 1451, 1406, 1294, 1169, 1108, 983, and 810 wave numbers. Thermomechanical analylsis (TMA) was performed on a cured sample of this monomer. It was found to have a glass transition ($T_g$) of 53.8° C., an $\alpha_1$=57.6 ppm/° C., and an $\alpha_2$=175.1 ppm/° C.

Example 8

Preparation of Compound 3

A two-neck, 500 mL flask was charged with 28.84 g (0.20 mole) Unoxol Diol, 78.4 g (0.40 mole) tricyclclodecanediol, 3.0 g sulfuric acid, and 40 mL heptane. This mixture was refluxed under an argon blanket at 145° C. to collect 8.2 mL water. The mixture was cooled and 16.2 g acrylic acid, 19.4 g methacrylic acid, 200 mL heptane and 210 mg hydroquinone. The new mixture was refluxed under an air sparge for three hours to collect 7.8 mL of water. The usual work up provided 105.2 g of a viscous, clear, brown liquid. The 5 rpm viscosity of this product was 2,271 centipoises at 25.0° C. A TGA (10° C. per minute, air purge) run on the neat monomer had 92.8% residual weight at 300° C. The TGA was repeated on the sample with 2% added dicumyl peroxide catalyst and the residual weight at 300° C. was 97.4% with a decomposition onset temperature of 431.2° C. A DSC was run on the catalyzed sample and a mono-modal cure exotherm was observed with an onset temperature of 135.5° C., a cure peak at 144.2° C., and a cure energy of 172.1 joules per gram. An FTIR run on this product had prominent absorptions at 2940, 1721, 1637, 1451, 1406, 1294, 1165, 1110, 1055, 983, and 810 wave numbers. Thermomechanical analylsis (TMA) was performed on a cured sample of this monomer. It was found to have a glass transition ($T_g$) of 71.5° C., an $\alpha_1$=59.7 ppm/° C., and an $\alpha_2$=185.0 ppm/° C.

Example 9

Preparation of Compound 7

A 500 mL, 1-neck flask was charged with 40 g of a 50% NaOH aqueous solution, 58.8 g (0.30 mole) tricyclodecane dimethanol, 46.0 g (0.20 mole) 1,5-dibromopentane, 100 mL toluene and 1.5 g tetramethylammonium bromide. This mixture was magnetically stirred at 50° C. for twenty-four hours. The mixture was extracted with 5×25 mL deionized water and then dried with twelve grams of magnesium sulfate. The solution was filtered and then placed in a 500 mL, 2-neck flask along with 18.0 g (0.25 mole) acrylic acid, 21.5 g (0.25 mole) methacrylic acid, 2.0 g of methanesulfonic acid, and 170 mg of hydroquinone. A air inlet tube, Dean Stark trap and condenser were attached and this mixture was refluxed under an air sparge for 2.5 hours and 7.0 mL of water was collected in the trap. The mixture was neutralized with aqueous sodium bicarbonate, dried with magnesium sulfate and then passed over 50 g of silica gel. The product was a clear brown liquid that weighed 78.53 g. A TGA (10° C. per minute, air purge) run on the neat monomer had 75.0% residual weight at 300° C. The TGA was repeated on the sample with 2% added dicumyl peroxide catalyst and the residual weight at 300° C. was 90.4% with a decomposition onset temperature of 294.3° C. A DSC was run on the catalyzed sample and a mono-modal cure exotherm was observed with an onset temperature of 143.7° C., a cure peak at 148.7° C., and a cure energy of 127.6 joules per gram. An FTIR run on this product had prominent absorptions at 2944, 2862, 1719, 1637, 1454, 1295, 1166, 1110, 982, and 811 wave numbers.

Example 10

Preparation of Compound 8

A 500 mL, 2-neck flask was charged with 40 g of a 50% NaOH aqueous solution, 58.8 g (0.30 mole) tricyclodecane dimethanol, 19.8 g (0.20 mole) 1,2-dichloroethane, 100 mL toluene and 1.5 g tetramethylammonium bromide. This mixture was magnetically stirred at 65° C. for 64 hours. The mixture was extracted with 5×25 mL deionized water and then dried with twelve grams of magnesium sulfate. The solution was filtered and then placed again into a 500 mL, 2-neck flask along with 18.0 g (0.25 mole) acrylic acid, 21.5 g (0.25 mole) methacrylic acid, 2.0 g of methanesulfonic acid, and 80 mg of hydroquinone. A air inlet tube, Dean Stark trap and condenser were attached and this mixture was refluxed under an air sparge for 2.0 hours and 7.8 mL of water was collected in the trap. The mixture was neutralized with aqueous sodium bicarbonate, dried with magnesium sulfate and then passed over 25 g of silica gel. The product was a clear, light brown liquid that weighed 77.3 g. A TGA (10° C. per minute, air purge) run on the neat monomer had 90.1% residual weight at 300° C. The TGA was repeated on the sample with 2% added dicumyl peroxide catalyst and the residual weight at 300° C. was 96.8% with a decomposition onset temperature of 410.0° C. A DSC was run on the catalyzed sample and a mono-modal cure exotherm was observed with an onset temperature of 141.1° C., a cure peak at 150.5° C., and a cure energy of 222.6 joules per gram. An FTIR run on this product had prominent absorptions at 2947, 2877, 1716, 1637, 1407, 1294, 1160, 1054, 982, and 810 wave numbers.

Example 11

Preparation of Compound 9

A 500 mL, 2-neck flask was charged with 40 g of a 50% NaOH aqueous solution, 58.8 g (0.30 mole) tricyclodecane dimethanol, 25.4 g (0.20 mole) 1,4-dichlorobutane, 100 mL toluene and 1.5 g tetramethylammonium bromide. This mixture was magnetically stirred at 65° C. for 24.5 hours. The mixture was extracted with 5×25 mL deionized water and then dried with twelve grams of magnesium sulfate. The solution was filtered and then placed again into a 500 mL, 2-neck flask along with 18.0 g (0.25 mole) acrylic acid, 21.5 g (0.25 mole) methacrylic acid, 2.0 g of methanesulfonic acid, and 85 mg of hydroquinone. An air inlet tube, Dean Stark trap and condenser were attached and this mixture was refluxed under an air sparge for 2.5 hours and 7.6 mL of water was collected in the trap. The mixture was neutralized with aqueous sodium bicarbonate, dried with magnesium sulfate and then passed over 25 g of silica gel. The product was a clear, light brown liquid that weighed 84.3 g. A TGA (10° C. per minute, air purge) run on the neat monomer had 96.3% residual weight at 300° C. The TGA was repeated on the sample with 2% added dicumyl peroxide catalyst and the residual weight at 300° C. was 96.7% with a decomposition onset temperature of 332.6° C. A DSC was run on the catalyzed sample and a mono-modal cure exotherm was observed with an onset temperature of 138.6° C., a cure peak at 148.7° C., and a cure energy of 186.1 joules per gram. An FTIR run on this product had prominent absorptions at 2945, 2873, 1715, 1637, 1452, 1406, 1294, 1159, 983, and 810 wave numbers.

Examples 12-17

Silver-Filled Adhesive Compositions

Silver filled adhesive compositions were made according to the formula:

TABLE 1

Generic Conductive Thermoset Adhesive Test Compositions

| Component | Raw Material | Percentage |
|---|---|---|
| 1 | Test Oligomer (following examples) | 11.12 |
| 2 | SR324[a] | 1.586 |
| 3 | SR239[a] | 1.84 |
| 4 | Ricon130MA20[a] | 1.43 |
| 5 | Coupling Agent | 0.61 |
| 6 | SME-OH[b] | 0.53 |
| 7 | o,o'-Diallyl BPA | 0.36 |
| 8 | Dicumyl Peroxide | 0.35 |
| 9 | KR39-40B[c] | 0.09 |
| 10 | A6177[d] | 0.09 |
| 11 | Silver Flake | 82.00 |

[a]thermoset monomers available from Sartomer;
[b]epoxy-methacrylate hybrid monomer;
[c]resin anti-bleed additive;
[d]conductivity promoter

TABLE 2

Test Monomers Used According to the Table 1 Formula

| Test Monmer | Example | | | | | |
|---|---|---|---|---|---|---|
| | 12 | 13 | 14 | 15 | 16 | 17 |
| R-1111[a] | 100% | | 50% | | | |
| Example 1 | | 100% | 50% | | | |
| Example 2 | | | | 100% | | |
| Example 3 | | | | | 100% | |
| Example 4 | | | | | | 100% |

[a]difunctional acrylate monomer

TABLE 3

Test Results for Experimental Compositions

| Test Parameter | Example | | | | | |
|---|---|---|---|---|---|---|
| | 12 | 13 | 14 | 15 | 16 | 17 |
| 5 rpm Viscosity@ 25° C.[a] | 12,000 | 6,062 | 8,355 | 7,127 | 6,471 | 13,020 |
| Thixotropic Index[b] | 5.5 | 6.6 | 6.7 | 6.2 | 5.8 | 6.1 |
| RT Shear (150 mil² die)[c] | | | | | | |
| Ag on Cu | 26.7 ± 4.9 | 34.1 ± 4.3 | 20.0 ± 4.5 | 24.1 ± 5.8 | 28.4 ± 4.9 | 28.0 ± 7.6 |
| Cu | 21.5 ± 1.6 | 21.4 ± 3.4 | 23.3 ± 6.0 | 34.5 ± 2.3 | 30.1 ± 4.0 | 40.5 ± 5.5 |
| Ni/Pd/Au | 26.6 ± 2.7 | 34.8 ± 5.6 | 28.9 ± 4.6 | 41.7 ± 4.4 | 32.1 ± 6.5 | 48.3 ± 5.4 |

TABLE 3-continued

Test Results for Experimental Compositions

| Test Parameter | Example | | | | | |
|---|---|---|---|---|---|---|
| | 12 | 13 | 14 | 15 | 16 | 17 |
| 260° C. Shear (300 mil² die)[c] | | | | | | |
| Ag on Cu | 39.8 + 9.1 | 21.3 + 1.3 | 14.2 + 2.7 | 17.7 + 5.2 | 21.6 + 3.7 | 19.3 + 6.6 |
| Cu | 24.5 + 5.3 | 25.5 + 4.4 | 27.3 + 7.8 | 36.3 + 6.1 | 36.7 + 8.8 | 30.9 + 6.4 |
| Ni/Pd/Au | 38.7 + 7.3 | 32.8 + 5.9 | 32.4 + 5.1 | 46.9 + 4.5 | 35.9 + 8.8 | 37.4 + 4.7 |
| 260° C. Shear (300 mil2 die)[c] after 5 hour water boil[d] | | | | | | |
| Ag on Cu | 33.8 + 5.8 | 19.6 + 4.7 | 19.7 + 2.1 | 15.7 + 3.6 | 18.3 + 3.8 | 17.1 + 3.1 |
| Cu | 30.8 + 2.0 | 22.0 + 4.7 | 26.8 + 6.5 | 29.3 + 8.1 | 30.8 + 7.9 | 25.2 + 11 |
| Ni/Pd/Au | 39.8 + 8.3 | 35.8 + 9.4 | 32.9 + 8.2 | 1.1 + 0.5 | 24.0 + 8.0 | 36.3 + 6.8 |
| Volume Resistivity[e] | | | | | | |
| Initial | 0.00024 | 0.00004 | 0.000094 | 0.000055 | 0.000043 | 0.000211 |
| Following 175° C. bake[f] | 0.000102 | 0.000027 | 0.000050 | 0.000039 | 0.000029 | 0.000133 |

[a]centipoises;
[b]0.5/5 rpm viscosity ratio;
[c]die shear values in kilograms force for bare silicon die on leadframe types as indicated;
[d]accelerated moisture resistance test;
[e]Ohm-cm;
[f]simulates post-mold-cure conditions.

The composition of Example 12 provided the control for these Examples. The adhesion of the other experimental compositions (with the notable exception of post boil adhesion of Example 15 on the Ni/Pd/Au plated leadframes), were all generally comparable to that of the control. The post-bake electrical resistance of compositions of Examples 13, 14, 15, and 16 were 26%, 50%, 38% and 29% that of the control, respectively. The viscosities of the Example 13, 15, and 16 compositions were much lower than that of the control and significantly more silver could be added to further enhance the electrical conductivity benefit of the polyether oligomers of this invention when compared to the control. The post-bake electrical resistance and viscosity of composition of Example 17 was no lower than the control, but it did have superior adhesion on small silicon die.

Examples 18-21

Additional Silver-Filled Adhesives Compositions

Another set of silver-filled compositions was prepared using invention compounds as indicated below in Table 4. The nature of those compositions and the corresponding test results are summarized in Table 4.

TABLE 4

Test Results for Experimental Compositions

| | Example 18 | Example 19 | Example 20 | Example 21 |
|---|---|---|---|---|
| R-1111[a] | 8.17 | | | |
| Example 9 | | 8.17 | | |
| Example 10 | | | 8.17 | |
| Example 11 | | | | 8.17 |
| Maleimide Oligomer[b] | 1.23 | 1.23 | 1.23 | 1.23 |
| Dicumyl Peroxide | 0.54 | 0.54 | 0.54 | 0.54 |
| Coupling Agent | 0.68 | 0.68 | 0.68 | 0.68 |
| 2MAOK Epoxy Catalyst | 0.07 | 0.07 | 0.07 | 0.07 |
| Epoxy Monomer[c] | 2.7 | 2.7 | 2.7 | 2.7 |
| SR335[d] | 5.45 | 5.45 | 5.45 | 5.45 |
| CD535[d] | 2.16 | 2.16 | 2.16 | 2.16 |
| Antibleed | 0.1 | 0.1 | 0.1 | 0.1 |
| PM4165[e] | 40% | 40% | 40% | 40% |
| PM4166[e] | 45% | 45% | 45% | 45% |
| Viscosity (cps, 1 rpm) | 59800 | 43410 | 31940 | 33580 |
| Viscosity (cps, 5 rpm) | 9666 | 7946 | 6062 | 6389 |
| Thixotropic Index | 6.2 | 5.5 | 5.3 | 5.3 |
| Volume resistivity[f] (after cure) | 0.00016 | 0.000025 | 0.00005 | 0.00005 |
| Volume resistivity (after PMC[g]) | 0.00009 | 0.000025 | 0.00005 | 0.00005 |
| 270° C. DSS[h], | | | | |

TABLE 4-continued

Test Results for Experimental Compositions

|  | Example 18 | Example 19 | Example 20 | Example 21 |
|---|---|---|---|---|
| 200 × 200 mil die, PMC |  |  |  |  |
| Cu | 5.3 ± 0.9 | 2.6 ± 0.8 | 12.7 ± 2.9 | 9.6 ± 3.2 |
| Ag on Cu | 15.2 ± 3.3 | 2.9 ± 0.3 | 12.6 ± 1.4 | 10.4 ± 2.3 |
| Ni/Pd/Au | 11.9 ± 2.0 | 2.1 ± 0.4 | 16.6 ± 3.5 | 12.4 ± 2.4 |

[a] Difunctional acrylate monomer;
[b] polymaleimide monomer;
[c] diglycidyl epoxy monomer;
[d] thermoset monomers from Sartomer Corporation;
[e] silver flake;
[f] Ohm-cm;
[g] post-mold-cure simulation;
[h] die shear strength in kilograms force for bare silicon die on leadframe types as indicated.

The results presented in Table 4 further demonstrated improved electrical conductivity of adhesive compositions containing the polyether oligomers of this invention as compared a control maleimide monomer. The post mold cure electrical resistance of compositions of Examples 19, 20, and 21 were 28%, 56%, and 56% that of the control, respectively. The viscosities of the Example 19, and especially Examples 20 and 21 compositions were much lower than that of the control and accordingly, significantly more silver could be added to further enhance the electrical conductivity benefit of the polyether oligomers of this invention when compared to the control.

The adhesion of Example 19 was inferior to the control on all leadframe types. The adhesion for Examples 20 and 21 was lower than the control on silver leadframes, but both of these compositions were superior to the control on Cu and Ni/Pd/Ag leadframes.

What is claimed is:

1. An oligomer represented by structural formula I:

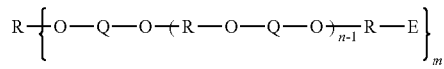

wherein:
each of R and Q is a moiety independently selected from the group consisting of a substituted or an unsubstituted aliphatic, aryl and heteroaryl;
m is an integer having a value between 1 and 4;
n is an integer having a value between 1 and about 10; and
each E is a moiety independently selected from the group consisting of acrylate, methacrylate, maleimide, styrenic, vinyl ester, olefin, allyl, vinyl ether, itaconate, fumarate, epoxy, oxetane, oxazoline, benzoxazine, cyanate ester and propargyl ether,
with the further proviso that when R or Q is a substituted aryl, the substitutent in the substituted aryl is selected from the group consisting of an alkyl, an alkenyl, an alkynyl, hydroxy, oxo, an alkoxy, mercapto, a cycloalkyl, a substituted cycloalkyl, a heterocyclic, a substituted heterocyclic, an aryl, a substituted aryl, a heteroaryl, a substituted heteroaryl, an aryloxy, a substituted aryloxy, a halogen, a haloalkyl, cyano, nitro, nitrone, an amino, an amido, —C(O)H, —S—, —S(O)$_2$—, —OC(O)—O—, —NR'—C(O)—, —NR'—C(O)—NR'—, —OC(O)—NR'—, wherein R' is selected from the group consisting of H, a lower alkyl, an acyl, an oxyacyl, carboxyl, carbamate, sulfonyl, sulfonamide and sulfuryl.

2. The oligomer of claim1, wherein R is selected from the group consisting of a substituted or an unsubstituted cycloalkyl having between 3 and about 30 carbon atoms.

3. The oligomer of claim 1, wherein R is selected from the group consisting of a substituted or an unsubstituted cycloalkyl having between 5 and about 15 carbon atoms.

4. The oligomer of claim 1, wherein R is selected from the group consisting of a substituted or an unsubstituted cycloalkyl having between 6 and about 12 carbon atoms.

5. The oligomer of claim 1, wherein R is selected from the group consisting of a substituted or an unsubstituted cyclopentyl, cyclohexyl, norbornyl, tetracyclododecyl and dicyclopentadienyl.

6. The oligomer of claim 1, wherein Q is selected from the group consisting of a substituted or an unsubstituted aryl having between 6 and about 20 carbon atoms, a substituted cycloalkyl and an unsubstituted cycloalkyl.

7. The oligomer of claim 1, having a structure selected from the group consisting of structures represented by structural formulae II, III and IV:

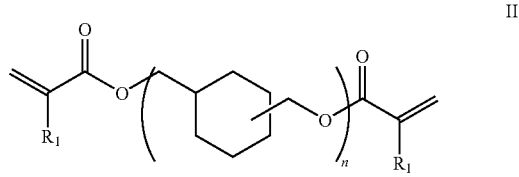

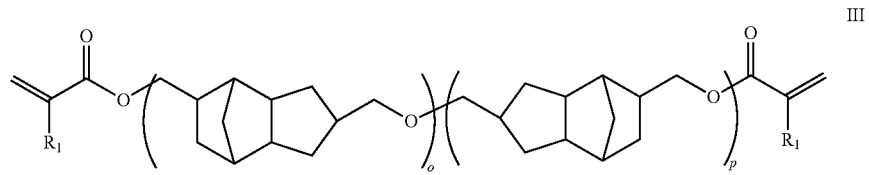

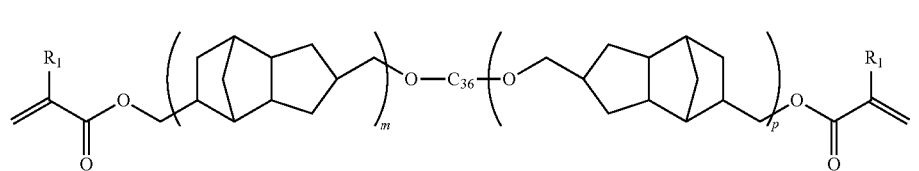

wherein:

in each of the formulae II, III and IV, $R_1$ is independently selected from the group consisting of H and methyl;

each of n, m and p is an integer independently having a value between 1 and 10;

o is an integer such that the sum of (o+p) has a value between 1 and 10; and $C_{36}$ is a dimer diol residue.

8. The oligomer of claim 7, wherein the oligomer is represented by structural formula III and the sum of (o+p) is between 2 and 5.

9. A compound selected from the group consisting of:

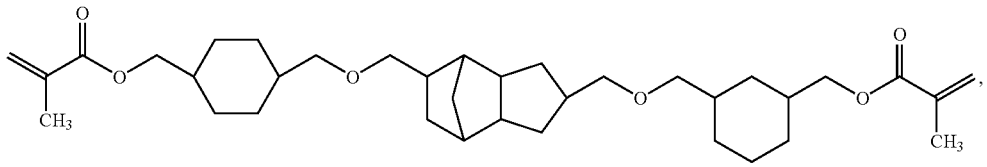

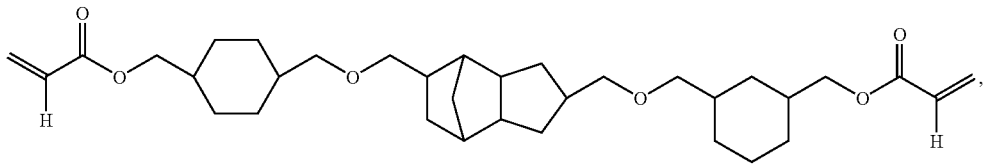

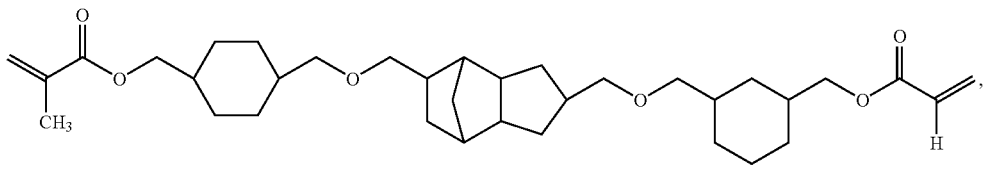

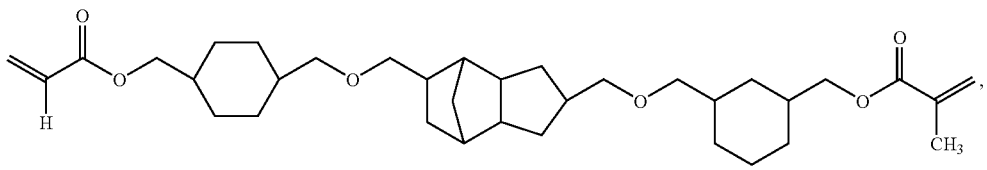

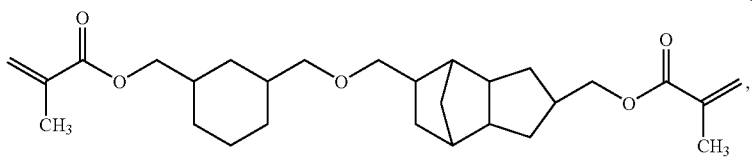

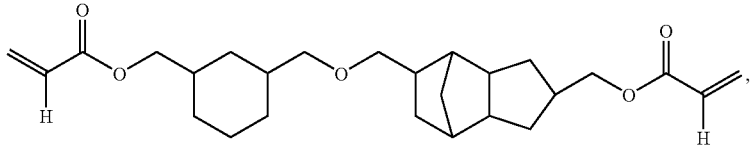

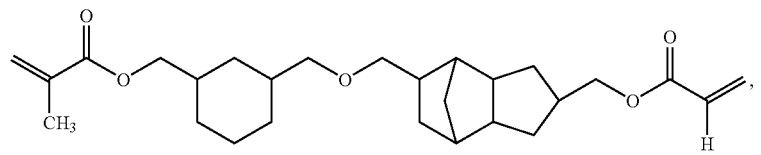
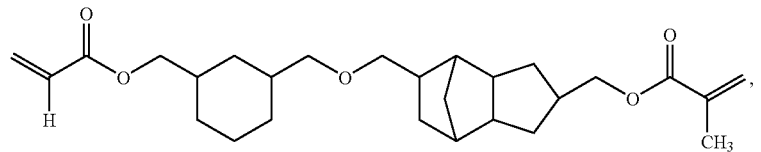
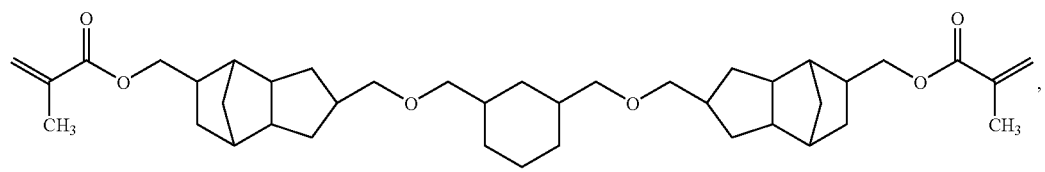
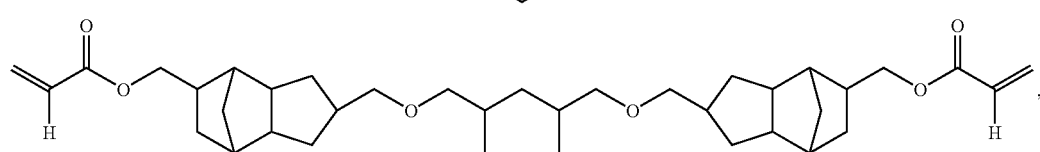
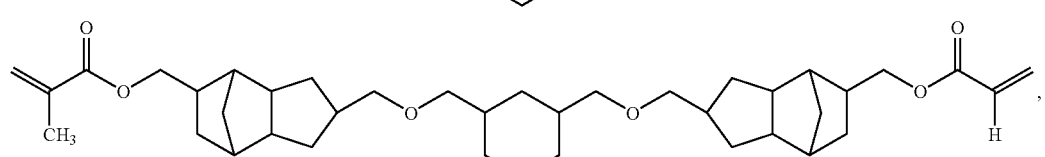
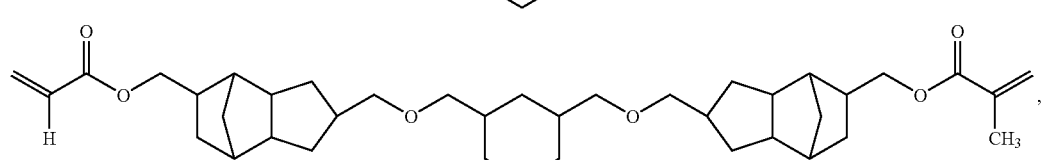
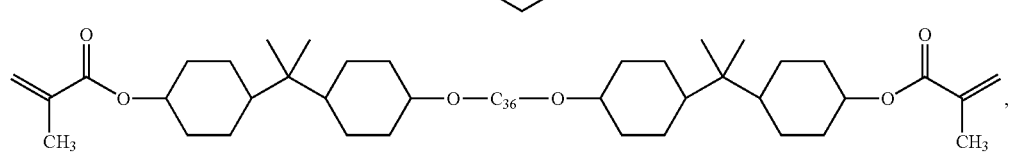
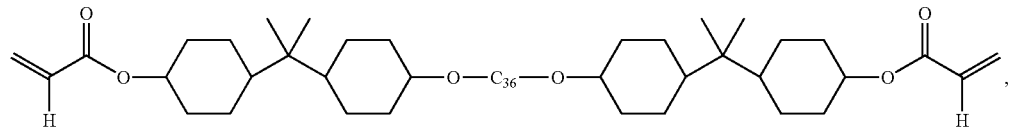
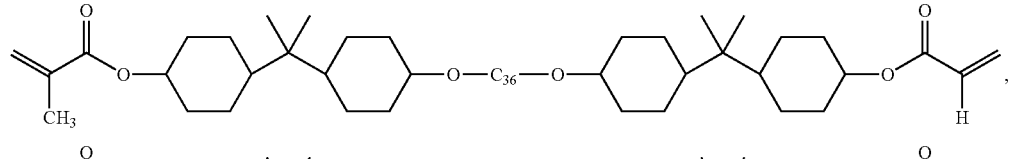
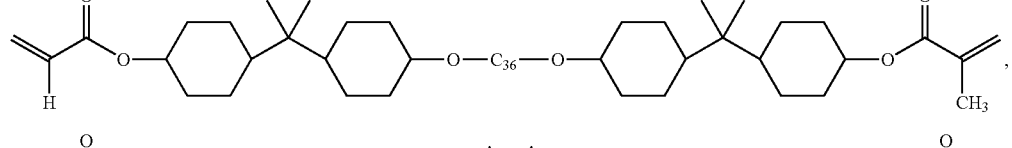
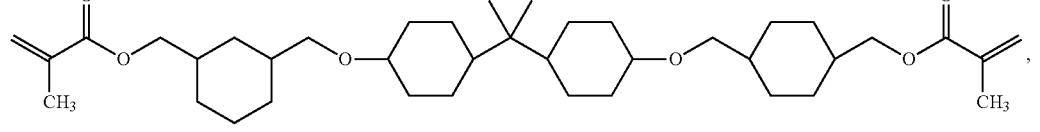

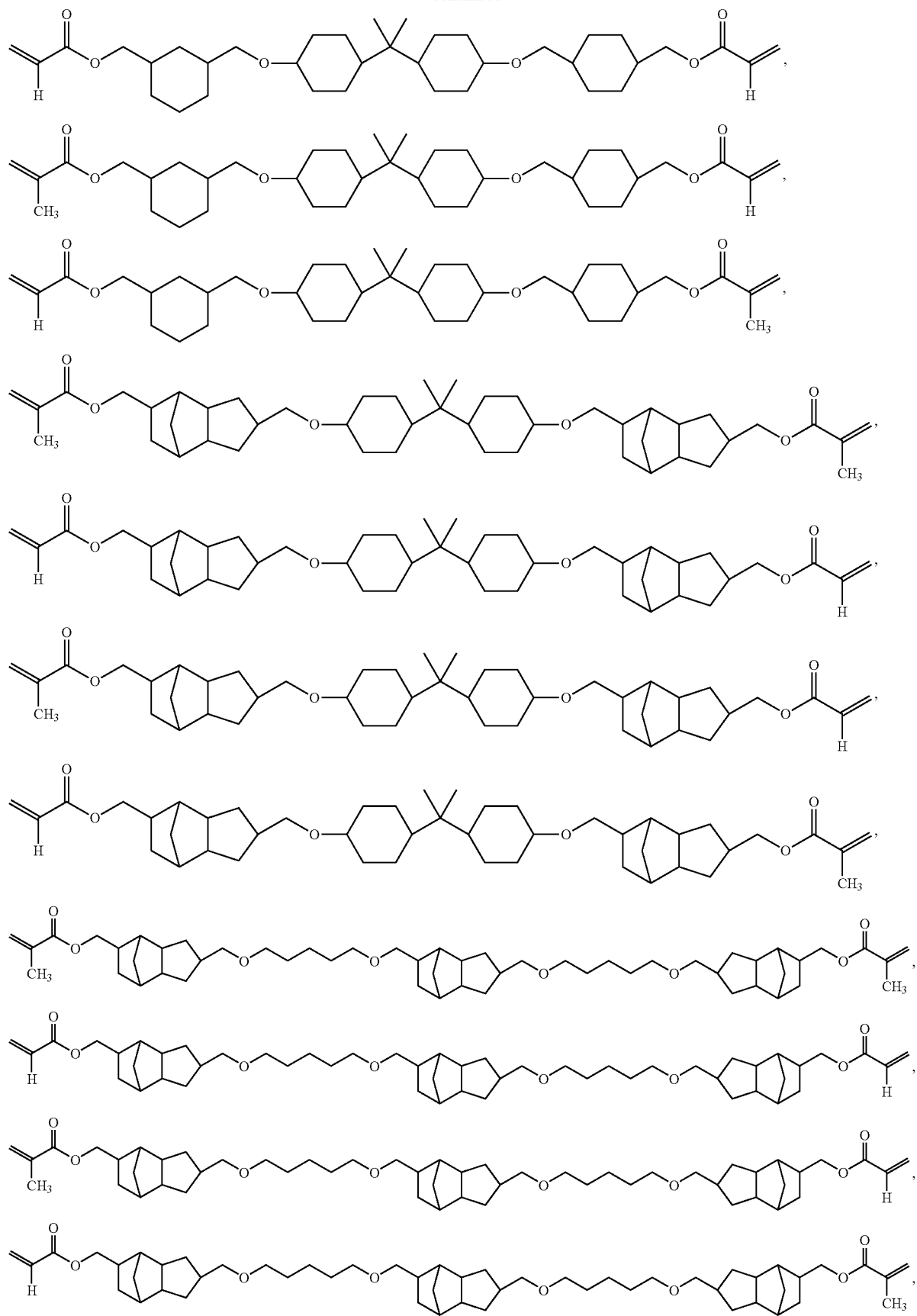

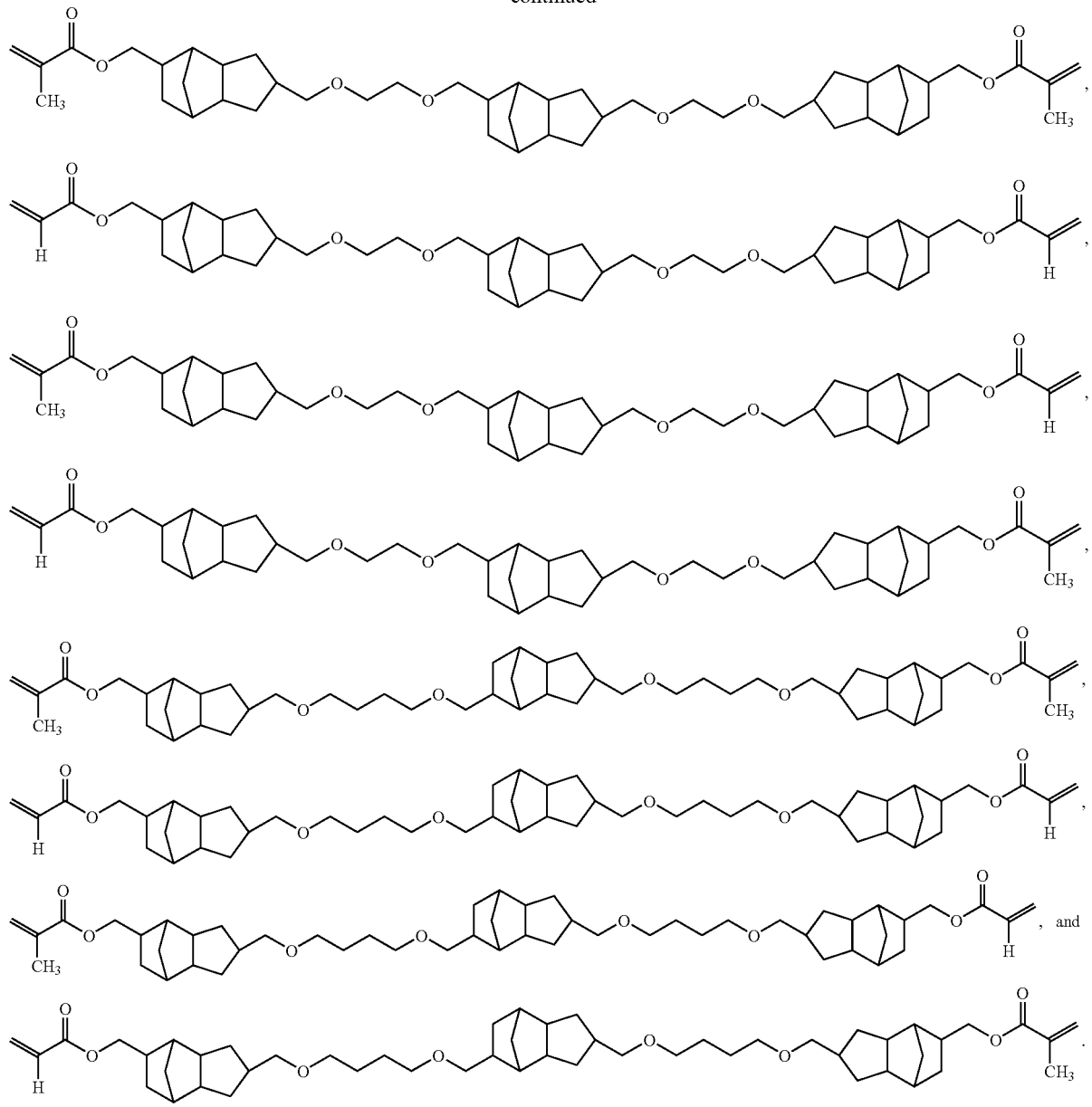

10. An adhesive composition comprising at least one oligomer of claim 1, and at least one curing initiator.

11. The adhesive composition of claim 10, wherein the at least one curing initiator comprises between about 0.1 wt % and about 5 wt % of the total weight of the composition.

12. The adhesive composition of claim 10, further comprising at least one additional compound selected from the group consisting of an acrylate, a methacrylate, a maleimide, a vinyl ether, a vinyl ester, a styrenic compound and an allyl functional compound.

13. The adhesive composition of claim 10, further comprising at least one of a reactive diluent and a filler.

14. The adhesive composition of claim 13, wherein the filler is thermally or electrically conductive.

15. The adhesive composition of claim 13, wherein the filler comprises silver.

16. The adhesive composition of claim 10, wherein the curing initiator comprises a free-radical initiator, a photoinitiator or both a free-radical initiator and a photoinitiator.

17. An adhesive composition comprising:
  a) between about 0.5 weight percent (wt %) and about 98 wt % of at least one oligomer of claim 1;
  b) between about 0 and about 90 wt % of a filler;
  c) between about 0.1 wt % and about 5 wt % of at least one curing initiator; and
  d) between about 0.1 wt % and about 4 wt % of at least one coupling agent,
  wherein each wt % is based on the total weight of the composition.

18. The adhesive composition of claim 17, wherein the at least one oligomer has a structure represented by structural formula II:

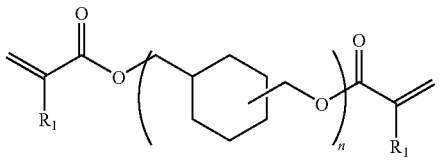

wherein $R_1$ is selected from the group consisting of H and methyl, and n is an integer having a value between 1 and 10.

19. The adhesive composition of claim 18, wherein the adhesive composition has an electrical resistance of less than about 0.0001 Ohm-cm.

20. The adhesive composition of claim 17, wherein the coupling agent is selected from the group consisting of a silicate ester, a metal acrylate salt and a titanate.

21. The adhesive composition of claim 17, wherein the at least one curing initiator is a peroxide.

22. The adhesive composition of claim 17, further comprising at least one additional compound selected from the group consisting of an acrylate, a methacrylate, a maleimide, a vinyl ether, a vinyl ester, a styrenic compound and allyl functional compounds.

23. An assembly comprising a first article adhered to a second article by a cured aliquot of the adhesive composition of claim 17.

24. A method for adhesively attaching a first article to a second article comprising
   a) applying an aliquot of the adhesive composition of claim 10 to the first article, the second article or both the first and second articles;
   b) contacting the first article and the second article, wherein the first article and the second article are separated only by the adhesive composition applied in step a); and
   c) curing the adhesive composition applied in step a), thereby adhesively attaching the first article to the second article.

25. The method of claim 24, wherein the first article and the second article are each independently selected from a memory device, an ASIC device, a microprocessor, a copper lead frame, an Alloy 42 lead frame, a semiconductor die and a substrate.

26. A method for at least one of:
   a) increasing the conductivity;
   b) reducing the electrical resistance; or
   c) reducing the viscosity of a thermoset adhesive comprising replacing at least one monomer in the thermoset adhesive with at least one polyether oligomer of claim 1.

27. The method of claim 26, further comprising increasing the amount of conductive metal in the thermoset adhesive composition.

28. An oligomer represented by structural formula I:

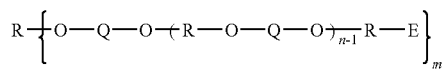

wherein:

each R is selected from the group consisting of a substituted or an unsubstituted cycloalkyl having between 3 and about 30 carbon atoms.

each Q is a moiety independently selected from the group consisting of a substituted or an unsubstituted aliphatic, aryl and heteroaryl;

m is an integer having a value between 1 and 4;

n is an integer having a value between 1 and about 10; and each E is a moiety independently selected from the group consisting of acrylate, methacrylate, maleimide, styrenic, vinyl ester, olefin, allyl, vinyl ether, itaconate, fumarate, epoxy, oxetane, oxazoline, benzoxazine, cyanate ester and propargyl ether.

29. The oligomer of claim 28, wherein R is selected from the group consisting of a substituted or an unsubstituted cycloalkyl having between 5 and about 15 carbon atoms.

30. The oligomer of claim 28, wherein R is selected from the group consisting of a substituted or an unsubstituted cycloalkyl having between 6 and about 12 carbon atoms.

31. The oligomer of claim 28, wherein R is selected from the group consisting of a substituted or an unsubstituted cyclopentyl, cyclohexyl, norbornyl, tetracyclododecyl and dicyclopentadienyl.

32. The oligomer of claim 28, having a structure selected from the group consisting of structures represented by structural formulae II, III and IV:

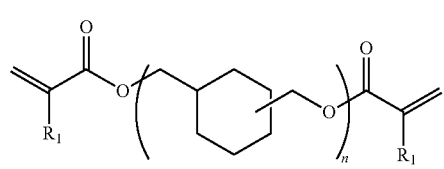

-continued

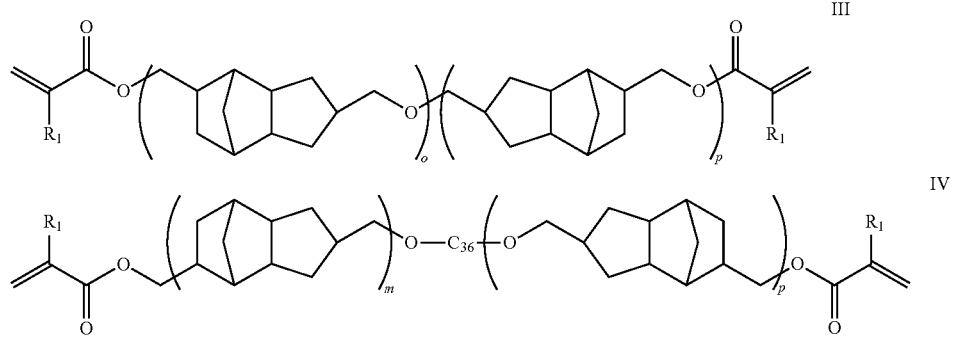

wherein:
in each of the formulae II, III and IV, $R_1$ is independently selected from the group consisting of H and methyl;

each of n, m and p is an integer independently having a value between 1 and 10;

o is an integer such that the sum of (o+p) has a value between 1 and 10; and $C_{36}$ is a dimer diol residue.

33. The oligomer of claim 32, wherein the oligomer is represented by structural formula III and the sum of (o+p) is between 2 and 5.

34. An adhesive composition comprising at least one oligomer of claim 28, at least one curing initiator and a filler comprising silver.

35. An adhesive composition comprising:
a) between about 0.5 weight percent (wt %) and about 98 wt % of at least one oligomer of claim 28;
b) between about 0 and about 90 wt % of a filler;
c) between about 0.1 wt % and about 5 wt % of at least one curing initiator; and
d) between about 0.1 wt % and about 4 wt % of at least one coupling agent, wherein each wt % is based on the total weight of the composition.

36. The adhesive composition of claim 35, wherein the at least one oligomer has a structure represented by structural formula II:

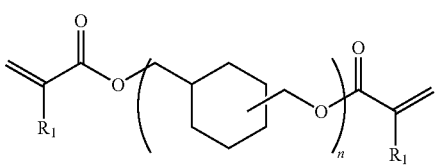

wherein $R_1$ is selected from the group consisting of H and methyl, and n is an integer having a value between 1 and 10.

37. The adhesive composition of claim 36, wherein the adhesive composition has an electrical resistance of less than about 0.0001 Ohm-cm.

38. The adhesive composition of claim 35, wherein the coupling agent is selected from the group consisting of a silicate ester, a metal acrylate salt and a titanate.

39. The adhesive composition of claim 35, wherein the at least one curing initiator is a peroxide.

40. The adhesive composition of claim 35, further comprising at least one additional compound selected from the group consisting of an acrylate, a methacrylate, a maleimide, a vinyl ether, a vinyl ester, a styrenic compound and allyl functional compounds.

41. An assembly comprising a first article adhered to a second article by a cured aliquot of the adhesive composition of claim 35.

* * * * *